US012806258B2

(12) United States Patent
Bernstein et al.

(10) Patent No.: US 12,806,258 B2
(45) Date of Patent: Nov. 24, 2026

(54) FORMULATIONS OF ACTIVATING ANTIGEN CARRIERS

(71) Applicant: STEMCELL TECHNOLOGIES CANADA INC., Vancouver (CA)

(72) Inventors: Howard Bernstein, Cambridge, MA (US); Defne Yarar, Watertown, MA (US); Katarina Blagovic, Cambridge, MA (US); Amritha Ramakrishnan, Watertown, MA (US); Maisam Dadgar, Cambridge, MA (US); Louise Clear, Watertown, MA (US); Jason Murray, Watertown, MA (US); Tarek Abdeljawad, Concord, MA (US); Claire Page, Watertown, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 1120 days.

(21) Appl. No.: 17/563,780

(22) Filed: Dec. 28, 2021

(65) Prior Publication Data

US 2022/0233676 A1 Jul. 28, 2022

Related U.S. Application Data

(60) Provisional application No. 63/131,457, filed on Dec. 29, 2020.

(51) Int. Cl.

| | |
|---|---|
| ***A61K 39/12*** | (2006.01) |
| ***A61K 39/39*** | (2006.01) |
| ***A61K 47/20*** | (2006.01) |
| *A61K 39/00* | (2006.01) |

(52) U.S. Cl.

CPC .............. *A61K 39/12* (2013.01); *A61K 39/39* (2013.01); *A61K 47/20* (2013.01); *A61K 2039/515* (2013.01); *A61K 2039/5156* (2013.01); *A61K 2039/55561* (2013.01)

(58) Field of Classification Search

None

See application file for complete search history.

(56) References Cited

U.S. PATENT DOCUMENTS

| | | | | |
|---|---|---|---|---|
| 8,512,941 | B2 | 8/2013 | Natan | |
| 9,562,075 | B2 * | 2/2017 | Van Der Burg | C12N 7/00 |
| 2002/0114791 | A1 * | 8/2002 | Crowe | A61P 7/04 514/178 |
| 2018/0142198 | A1 * | 5/2018 | Sharei | A61P 43/00 |
| 2018/0271910 | A1 | 9/2018 | Mata-Fink et al. | |
| 2019/0017072 | A1 * | 1/2019 | Ditommaso | C12N 5/0636 |

FOREIGN PATENT DOCUMENTS

| | | | | |
|---|---|---|---|---|
| WO | 2019178005 | A2 | 9/2019 | |
| WO | WO-2019178006 | A2 * | 9/2019 | A61K 40/11 |
| WO | 2020154696 | A1 | 7/2020 | |
| WO | 2020176789 | A1 | 9/2020 | |
| WO | 2022026621 | A1 | 2/2022 | |

OTHER PUBLICATIONS

Boersma et al., J Nucl Med, 2005, 46:2035-2050 (Year: 2005).*
The Journal for Immunotherapy of Cancer, Dec. 10, 2020, vol. 8, Suppl.3, A98-A99, 165.
Product Information, Catalog Nos. C3124, C2999, and C2874, Sigma-Aldrich, Nov. 2010.

* cited by examiner

*Primary Examiner* — Stacy B Chen
(74) *Attorney, Agent, or Firm* — Smart & Biggar LP; Micheline Gravelle

(57) ABSTRACT

The present application provides formulations of activating antigen carriers (AACs), wherein the formulation comprises: AACs comprise at least one antigen and an adjuvant and a cryopreservation medium.

18 Claims, 8 Drawing Sheets

Specification includes a Sequence Listing.

FORMULATIONS OF ACTIVATING ANTIGEN CARRIERS

CROSS REFERENCE TO RELATED APPLICATIONS

This application claims the benefit of U.S. Provisional Application No. 63/131,457, filed on Dec. 29, 2020, the entire contents of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322003400SEQLIST.TXT, date recorded: Dec. 23, 2021, size: 13,016 bytes).

FIELD OF THE INVENTION

The present disclosure relates generally to formulations of activating antigen carriers (AACs) comprising at least one antigen and an adjuvant, and a cryopreservation medium. Also provided are methods of manufacturing such AACs comprising the at least one antigen and the adjuvant, methods of formulating the cryopreservable formulation, and methods of cryopreserving the formulation.

BACKGROUND OF THE INVENTION

Papillomaviruses are small nonenveloped DNA viruses with a virion size of –55 nm in diameter. More than 100 human papillomavirus (HPV) genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN).

Many of the known HPV types cause benign lesions with a subset being oncogenic. Based on epidemiologic and phylogenetic relationships, HPV types are classified into fifteen "high-risk types" (HPV 16, 18, 31, 33, 35, 39, 45, 51, 52, 56, 58, 59, 68, 73, and 82) and three "probable high-risk types" (HPV 26, 53, and 66), which together are known to manifest as low and high grade cervical changes and cancers, as well as other anogenital cancers such as vulval, vaginal, penile, anal, and perianal cancer, as well as head and neck cancers. Recently, the association of high risk types HPV 16 and 18 with breast cancer was also described. Eleven HPV types classified as "low risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness *Am J Hematol Oncol* 13(6):20-27 (2017).

Immunotherapy can be divided generally into two main types of interventions, either passive or active. Passive protocols include administration of pre-activated and/or engineered cells (e.g., CAR T cells), disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous dendritic cell (DCs) as vehicles for tumor antigen delivery, and infusion of immune checkpoint modulators. See Papaioannou, Nikos E., et al. *Annals of translational medicine* 4.14 (2016). Adoptive immunotherapy can be employed to modulate the immune response, enhance antitumor activity, and achieve the goal of treating or preventing HPV-associated cancers.

$CD8^+$ cytotoxic T lymphocytes (CTL) and $CD4^+$ helper T (Th) cells stimulated by disease-associated antigens have the potential to target and destroy diseased cells; however, current methods for inducing endogenous T cell responses have faced challenges. The formulations and vials described herein comprise AACs in cryopreservation medium that can be manufactured, stored and transported without loss in functionality, before administration to individuals in need thereof. The methods described herein are used to efficiently generate AACs, which may be anucleate cells or anucleate cell-derived entities comprising at least one HPV antigen and an adjuvant, in a high throughput manner, which can be utilized in inducing a robust T cell response to the HPV antigens. The disclosure herein also describes methods, treatments, doses and regimens for treating individuals with HPV-associated cancers using AACs comprising HPV antigens and adjuvants.

All references cited herein, including patent applications and publications, are incorporated by reference in their entirety. The patent publications WO 2013/059343, WO 2015/023982, WO 2016/070136, WO2017041050, WO2017008063, WO 2017/192785, WO 2017/192786, WO 2019/178005, WO 2019/178006, WO 2020/072833, WO 2020/154696, and WO 2020/176789, US 20180142198, and US 20180201889 are hereby expressly incorporated by reference in their entirety.

BRIEF SUMMARY OF THE INVENTION

In some aspects, the invention provides a pharmaceutical formulation comprising activating antigen carriers (AACs), the formulation comprising a) AACs wherein the AACs comprise at least one antigen and an adjuvant, and b) a cryopreservation medium. In some embodiments, the formulation comprises about $0.5\times10^9$ AACs to about $1\times10^{10}$ AACs. In some embodiments, the formulation comprises about $7\times10^9$ AACs. In some embodiments, the formulation comprises about $7\times10^9$ AACs prior to freezing. In some embodiments, the formulation comprises about $9\times10^9$ AACs after thawing. In some embodiments, wherein the formulation comprises about $0.5\times10^9$ AACs/mL to about $1\times10^9$ AACs/mL. In some embodiments, the formulation comprises about $0.7\times10^9$ AACs/mL. In some embodiments, the formulation comprises about $0.7\times10^9$ AACs/mL prior to freezing. In some embodiments, the formulation comprises AACs that were previously frozen, wherein the formulation comprises about $1\times10^9$ AACs/mL after thawing. In some embodiments, the formulation comprises AACs that were previously frozen, wherein the formulation comprises about $1\times10^9$ AACs/mL after thawing as measured by flow cytometry. In some embodiments, the formulation comprises AACs that were previously frozen, wherein the formulation comprises about $0.7\times10^9$ AACs/mL after thawing as measured by Coulter counter.

In some embodiments of the invention, at least about 70%, 80%, 90%, or 95% of AACs of a population of the AACs in the formulation are functional. In some embodiments, the AACs in the formulation maintain equal to or greater than about 70% functionality. In some embodiments, the formulation comprises about $1\times10^8$ functional AACs/mL to about $1\times10^9$ functional AACs/mL. In some embodiments, wherein at least about 70%, 80%, 90%, or 95% of AACs of a population of the AACs are positive for annexin staining. In some embodiments, the AACs in the formulation maintain equal to or greater than about 70% are positive for annexin staining. In some embodiments, the annexin is annexin V.

In some embodiments of the invention, the cryopreservation medium in the formulation comprises dimethylsulfoxide (DMSO). In some embodiments, the cryopreservation medium comprises about 0.5% to about 5% DMSO. In some embodiments, the cryopreservation medium comprises about 2% DMSO. In some embodiments, the cryopreservation medium is CryoStor® CS2.

In some embodiments, the pH of the formulation is about 6.0 to about 8.5. In some embodiments, the pH of the formulation is about 7.6.

In some aspects, the invention provides a pharmaceutical formulation of AACs, the formulation comprising about $0.5\times10^9$ AACs to about $1\times10^{10}$ AACs in cryopreservation medium, wherein AACs comprise at least one antigen and an adjuvant, wherein the pH of the formulation is about pH 6.0 to about pH 8.5. In some embodiments, the formulation comprising about $0.5\times10^9$ AACs to about $1\times10^{10}$ AACs in a cryopreservation medium, wherein AACs comprise at least one antigen and an adjuvant, wherein the pH of the formulation is about pH 7.6. In some embodiments, formulation comprises about $7\times10^9$ AACs prior to freezing. In some embodiments, the formulation comprises AACs that were previously frozen, wherein the formulation comprises about $9\times10^9$ cells after thawing. In some embodiments, the formulation comprises about $0.5\times10^9$ AACs/mL to about $1\times10^9$ AACs/mL. In some embodiments, the formulation comprises about $0.7\times10^9$ AACs/mL. In some embodiments, the formulation comprises about $0.7\times10^9$ AACs/mL prior to freezing. In some embodiments, the formulation comprises AACs that were previously frozen, wherein the formulation comprises about $1\times10^9$ AACs/mL after thawing. In some embodiments, the formulation comprising about $7\times10^9$ AACs in about 9.5 mL of cryopreservation medium, wherein AACs comprise at least one antigen and an adjuvant, and wherein the pH of the formulation is about pH 7.6. In some embodiments, the cryopreservation medium is CryoStor® CS2. In some embodiments, wherein the formulation is sterile. In some embodiments, the formulation comprises less than about 2 EU/mL endotoxin. In some embodiments, the formulation is free of mycoplasma.

In some embodiments of the invention, the AACs of the formulation comprises the at least one human papillomavirus (HPV) antigen. In some embodiments, the HPV antigen is a HPV-16 antigen or a HPV-18 antigen. In some embodiments, the antigen comprises a peptide derived from HPV E6 and/or E7. In some embodiments, wherein the antigen comprises a peptide derived from HPV E6 and a peptide from HPV E7. In some embodiments, the antigen comprises the amino acid sequence of any one of SEQ ID NOs: 1-4. In some embodiments, the antigen comprises the amino acid sequence of any one of SEQ ID NOs:18-25. In some embodiments, the AACs comprises an antigen comprising the amino acid sequence of SEQ ID NO:19 and an antigen comprising the amino acid sequence of SEQ ID NO:23.

In some embodiments of the invention, the AACs of the formulation comprise an adjuvant, wherein the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist. In some embodiments, the adjuvant is a CpG 7909 oligodeoxynucleotide (ODN).

In some aspects of the invention, the formulation comprising AACs comprising the at least one antigen and an adjuvant are prepared by a process comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed anucleate cells; and b) incubating the perturbed anucleate cells with the at least one antigen and the adjuvant for a sufficient time to allow the at least one antigen and the adjuvant to enter the perturbed anucleate cells, thereby generating the AACs comprising the at least one antigen and the adjuvant. In some embodiments, the diameter of the constriction is about 1.6 μm to about 2.4 μm or about 1.8 μm to about 2.2 μm. In some embodiments, the input anucleate cell is a red blood cell.

In some aspects, the invention provides a vial comprising a pharmaceutical formulation; the pharmaceutical formulation comprising about $1\times10^9$ AACs to about $1\times10^{10}$ AACs in cryopreservation medium, wherein AACs comprise at least one antigen and an adjuvant, wherein the pH of the formulation is about pH 6.0 to about pH 8.5. In some aspects, the invention provides a vial comprising a pharmaceutical formulation; the pharmaceutical formulation comprising about $1\times10^9$ AACs to about $1\times10^{10}$ AACs in a cryopreservation medium, wherein AACs comprise at least one antigen and an adjuvant, wherein the pH of the formulation is about pH 7.6. In some embodiments, the formulation comprises about $7\times10^9$ AACs prior to freezing. In some embodiments, the formulation comprises AACs that were previously frozen, wherein the formulation comprises about $9\times10^9$ cells after thawing. In some embodiments, the formulation comprises AACs that were previously frozen, wherein the formulation comprises about $9\times10^9$ AACs after thawing as measured by flow cytometry. In some embodiments, the formulation comprises AACs that were previously frozen, wherein the formulation comprises about $7\times10^9$ AACs after thawing as measured by Coulter counter. In some embodiments, the formulation comprises about $0.5\times10^9$ AACs/mL to about $1\times10^9$ AACs/mL. In some embodiments, the formulation comprises about $0.7\times10^9$ AACs/mL. In some embodiments, the formulation comprises about $0.7\times10^9$ AACs/mL prior to freezing. In some embodiments, the formulation comprises AACs that were previously frozen, wherein the formulation comprises about $1\times10^9$ AACs/mL after thawing. In some embodiments, the formulation comprises AACs that were previously frozen, wherein the formulation comprises about $1\times10^9$ AACs/mL after thawing as measured by flow cytometry. In some embodiments, the formulation comprises AACs that were previously frozen, wherein the formulation comprises about $0.7\times10^9$ AACs/mL after thawing as measured by Coulter counter. In some embodiments, the invention provides a vial comprising a pharmaceutical formulation; the pharmaceutical formulation comprising about $7\times10^9$ AACs in about 9.5 mL of cryopreservation medium, wherein AACs comprise at least one antigen and an adjuvant, and wherein the pH of the formulation is about pH 7.6. In some embodiments, the AACs are in about 9.5 mL of the cryopreservation medium. In some embodiments, the pharmaceutical formulation comprises about $7\times10^9$ AACs in about 9.5 mL of cryopreservation medium, wherein AACs comprise at least one antigen and an adjuvant, and wherein the pH of the formulation is about pH 7.6. In some embodiments, the formulation is sterile.

In some aspects the invention provides a method of producing a pharmaceutical formulation of AACs, the method comprising adding a cryopreservation medium to the AACs wherein the AACs comprise at least one antigen and an adjuvant. In some aspects, the invention provides a method of producing a pharmaceutical formulation of AACs, wherein the AACs comprise the at least one antigen and an adjuvant, the method comprising: a) passing a cell suspension comprising a input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed anucleate cells; and b) incubating the perturbed anucleate cells with the at least one antigen and the adjuvant for a sufficient time to allow the at least one antigen and the adjuvant to enter the perturbed anucleate cells, thereby generating the AACs comprising the at least one antigen and the adjuvant; c) washing the AACs; and d) formulating the AACs in a cryopreservation medium. In some embodiments, the diameter of the constriction is about 1.6 μm to about 2.4 μm or about 1.8 μm to about 2.2 μm. In some embodiments, the AACs are washed about 6 times. In some embodiments, the AACs are washed by centrifugation and resuspension or by centrifugation and filtration. In some embodiments, the centrifugation is at about 4000 rpm. In some embodiments, about $1\times10^9$ AACs to about $1\times10^{10}$ AACs are formulated in about 9 mL to about 10 mL of the cryopreservation medium. In some embodiments, the pharmaceutical formulation comprises about $7\times10^9$ AACs prior to freezing. In some embodiments, the formulation comprises AACs that were previously frozen, wherein the formulation comprises about $9\times10^9$ cells after thawing. In some embodiments, the formulation comprises about $0.5\times10^9$ AACs/mL to about $1\times10^9$ AACs/mL. In some embodiments, the formulation comprises about $0.7\times10^9$ AACs/mL. In some embodiments, the formulation comprises about $0.7\times10^9$ AACs/mL prior to freezing. In some embodiments, the formulation comprises AACs that were previously frozen, wherein the formulation comprises about $1\times10^9$ AACs/mL after thawing as measured by flow cytometry. In some embodiments, the formulation comprises AACs that were previously frozen, wherein the formulation comprises about $0.7\times10^9$ AACs/mL after thawing as measured by Coulter counter. In some embodiments, about $7\times10^9$ AACs are formulated in about 10 mL of the cryopreservation medium. In some embodiments, the cryopreservation medium is CryoStor® CS2. In some embodiments, the input anucleate cell is a red blood cell.

In some embodiments, the method further comprises freezing the formulation of AACs at about −170 °C. In some embodiments, the formulation of AACs are frozen by a process comprising: a) placing the formulation in a chamber b) reducing the temperature of the chamber to about −3 °C, c) reducing the temperature of the chamber to about −140 °C at a rate of about −20 °C/minutes, d) reducing the temperature of the chamber to about −150 °C at a rate of about 1.5 °C/minutes, e) reducing the temperature of the chamber to about −170 °C at a rate of about 1.0 °C/minutes, and f) holding the temperature of the chamber at about −170 °C for at least about 10 minutes.

DETAILED DESCRIPTION OF THE INVENTION

Figure 1:
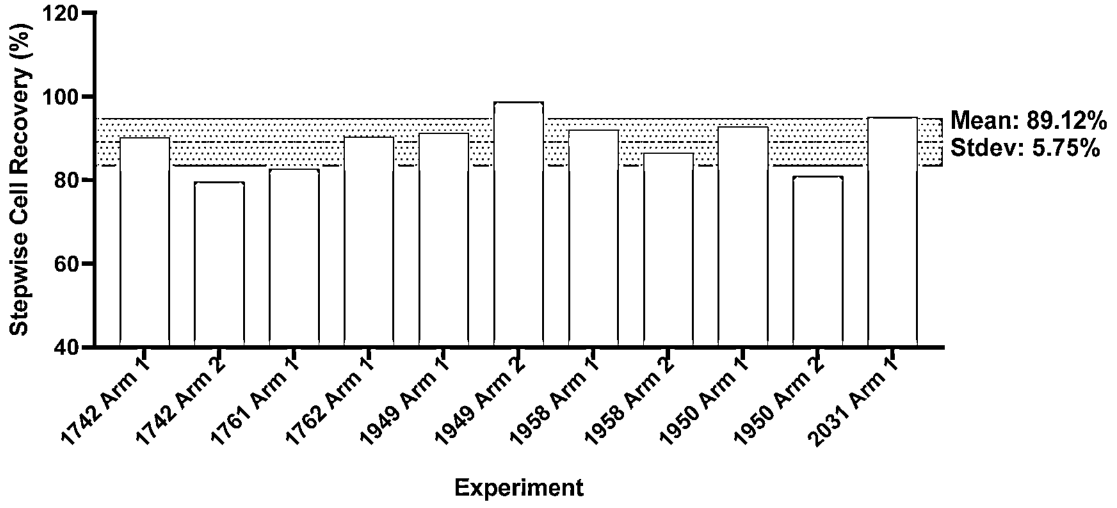
FIG. 1 shows an assessment of platelet removal and RBC recovery was performed over the LOVO process taken from seven different healthy donors.

In some aspects, the present invention provides a pharmaceutical formulation comprising AACs wherein the AACs comprise at least one antigen and an adjuvant, and a cryopreservation medium. In some embodiments, the present invention provides a pharmaceutical formulation of Activating Antigen Carriers (AACs), the formulation comprising about $0.5\times10^9$ AACs/mL to about $1\times10^{10}$ AACs/mL in a cryopreservation medium, wherein the AACs comprise at least one antigen and an adjuvant, wherein the pH of the formulation is about pH 7.6. In some embodiments, the formulation comprises $0.7\times10^9$ AACs/mL in a cryopreservation medium.

In some aspects, the present invention provides a vial comprising a pharmaceutical formulation; the pharmaceutical formulation comprising about $0.5\times10^9$ AACs/mL to about $1\times10^{10}$ AACs/mL in a cryopreservation medium (such as but not limited to CryoStor® CS2), wherein AACs comprise at least one antigen and an adjuvant, wherein the pH of the formulation is about pH 7.6.

In some aspects, the present invention provides a vial comprising a pharmaceutical formulation; the pharmaceutical formulation comprising about $0.7\times10^9$ AACs/mL in a cryopreservation medium (such as, but not limited to, CryoStor® CS2), wherein AACs comprise at least one antigen and an adjuvant, wherein the pH of the formulation is about pH 7.6.

Also provided are formulations and vials comprising AACs comprising at least one antigen and an adjuvant, and the methods of preparing the formulation of AACs comprising the at least one antigen and adjuvant. In some embodiments, the AACs are prepared by a process comprising: a) passing a cell suspension comprising a population of input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed input anucleate cells; and b) incubating the population of perturbed input anucleate cells with the at least one antigen and the adjuvant for a sufficient time to allow the at least one antigen to enter the perturbed input anucleate cells, thereby generating the AACs comprising the at least one antigen and the adjuvant. In some embodiments, the antigen is a HPV antigen. Also provided are compositions for use in inducing an immune response to HPV antigens or for treating a HPV-associated cancer. Also provided are uses of the formulation comprising an effective amount of the AACs in the manufacture of a medicament for stimulating an immune response to a HPV antigen or for treating a HPV-associated cancer.

In some embodiments, provided are methods of producing a pharmaceutical formulation of AACs, wherein the AACs comprise the at least one antigen and an adjuvant, the method comprising: a) passing a cell suspension comprising an input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed anucleate cells; and b) incubating the perturbed anucleate cells with the at least one antigen and the adjuvant for a sufficient time to allow the at least one antigen and the adjuvant to enter the perturbed anucleate cells, thereby generating the AACs comprising the at least one antigen and the adjuvant; c) washing the AACs; and d) formulating the AACs in a cryopreservation medium.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011)

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictates otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, "anucleate cell" refers to a cell lacking a nucleus. Such cells can include, but are not limited to, platelets, red blood cells (RBCs) such as erythrocytes and reticulocytes. Reticulocytes are immature (e.g., not yet biconcave) red blood cells, typically comprising about 1% of the red blood cells in the human body. Reticulocytes are also anucleate. In certain embodiments, the systems and methods described herein are used the treatment and/or processing of enriched (e.g., comprising a greater percentage of the total cellular population than would be found in nature), purified, or isolated (e.g., from their natural environment, in substantially pure or homogeneous form) populations of anucleate cells (e.g., RBCs, reticulocytes, and/or platelets). In certain embodiments, the systems and methods described herein are used for the treatment and/or processing of whole blood containing RBCs (e.g., erythrocytes or reticulocytes), platelets as well as other blood cells. Purification or enrichment of these cell types is accomplished using known methods such as density gradient systems (e.g., Ficoll-Hypaque), fluorescence activated cell sorting (FACS), magnetic cell sorting, or in vitro differentiation of erythroblasts and erythroid precursors.

The term "vesicle" as used herein refers to a structure comprising liquid enclosed by a lipid bilayer. In some examples, the lipid bilayer is sourced from naturally existing lipid composition. In some examples, the lipid bilayer can be sourced from a cellular membrane. In some examples, vesicles can be derived from various kinds of entities, such as cells. In such examples, a vesicle can retain molecules (such as intracellular proteins or membrane components) from the originating entity. For example, a vesicle derived from a red blood cell may contain any number of intracellular proteins that were in the red blood cell and/or membrane components of the red blood cell. In some examples, a vesicle can contain any number of molecules intracellularly in addition to the desired payload.

As used herein "payload" refers to the material that is being delivered into, such as loaded in, the anucleate cell-derived vesicle (e.g., an AAC). "Payload," "cargo," "delivery material," and "compound" are used interchangeably herein. In some embodiments, a payload may refer to a protein, a small molecule, a nucleic acid (e.g., RNA and/or DNA), a lipid, a carbohydrate, a macromolecule, a vitamin, a polymer, fluorescent dyes and fluorophores, carbon nanotubes, quantum dots, nanoparticles, and steroids. In some embodiments, the payload may refer to a protein or small molecule drug. In some embodiments, the payload may comprise one or more compounds.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

The term "exogenous" when used in reference to an agent, such as an antigen or an adjuvant, with relation to a cell or an AAC refers to an agent outside of the cell or an agent delivered into the cell from outside the cell. The cell may or may not have the agent already present, and may or may not produce the agent after the exogenous agent has been delivered.

The term "homologous" as used herein refers to a molecule which is derived from the same organism. In some examples the term refers to a nucleic acid or protein which is normally found or expressed within the given organism.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms. In some embodiments, an individual may be treated if they have a precancerous lesion, particularly a precancerous lesion associated with HPV infection.

As used herein, by "combination therapy" is meant that a first agent be administered in conjunction with another agent. "In conjunction with" refers to administration of one treatment modality in addition to another treatment modality, such as administration of a composition of nucleated cells as described herein in addition to administration of an immunoconjugate as described herein to the same individual. As such, "in conjunction with" refers to administration of one treatment modality before, during, or after delivery of the other treatment modality to the individual.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

In the context of cancer, the term "treating" includes any or all of killing cancer cells, inhibiting growth of cancer cells, inhibiting replication of cancer cells, lessening of overall tumor burden and ameliorating one or more symptoms associated with the disease.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In some examples, "modulate" refers to enhancing the presence or activity of a particular target. In some examples, "modulate" refers to suppressing the presence or activity of a particular target. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, gene editing and so forth. In other examples, inhibition of the expression of a protein may include, but not be limited to, reduction in the transcription of a nucleic acid encoding the protein, reduction in the stability of mRNA encoding the protein, inhibition of translation of the protein, reduction in stability of the protein, and so forth. In another example, inhibit may refer to the act of slowing or stopping growth; for example, retarding or preventing the growth of a tumor cell.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth. In other examples, suppression of the expression of a protein may include, but not be limited to, reduction in the transcription of a nucleic acid encoding the protein, reduction in the stability of mRNA encoding the protein, inhibition of translation of the protein, reduction in stability of the protein, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth. In other examples, enhancing the expression of a protein may include, but not be limited to, increase in the transcription of a nucleic acid encoding the protein, increase in the stability of mRNA encoding the protein, increase in translation of the protein, increase in the stability of the protein, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth. In other examples, inducing the expression of a protein may include, but not be limited to, increase in the transcription of a nucleic acid encoding the protein, increase in the stability of mRNA encoding the protein, increase in translation of the protein, increase in the stability of the protein, and so forth.

The term "polynucleotide" or "nucleic acid" as used herein refers to a polymeric form of nucleotides of any length, including ribonucleotides and deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. The backbone of the polynucleotide can comprise repeating units, such as N-(2-aminoethyl)-glycine, linked by peptide bonds (i.e., peptide nucleic acid). Alternatively, the backbone of the polynucleotide can comprise a polymer of synthetic subunits such as phosphoramidates and phorphorthioates and thus can be an oligodeoxynucleoside phosphoramidate ($P-NH_2$) or a mixed phosphorothioate-phosphorodiester oligomer or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" herein refer to DNA molecules of 10 to 30 nucleotides in length containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

As used herein, "microfluidic systems" refers to systems in which low volumes (e.g., mL, nL, pL, fL) of fluids are processed to achieve the discrete treatment of small volumes of liquids. Certain implementations described herein include multiplexing, automation, and high throughput screening. The fluids (e.g., a buffer, a solution, a payload-containing solution, or a cell suspension) can be moved, mixed, separated, or otherwise processed. In certain embodiments described herein, microfluidic systems are used to apply mechanical constriction to a cell suspended in a buffer, inducing perturbations in the cell (e.g., holes) that allow a payload or compound to enter the cytosol of the cell.

As used herein, a "constriction" may refer to a portion of a microfluidic channel defined by an entrance portion, a centerpoint, and an exit portion, wherein the centerpoint is defined by a width, a length, and a depth. In other examples, a constriction may refer to a pore or may be a portion of a pore. The pore may be contained on a surface (e.g., a filter and/or membrane).

For any of the structural and functional characteristics described herein, methods of determining these characteristics are known in the art.

Formulation of AACs Comprising Antigens

In some embodiments, provided is a pharmaceutical formulation comprising AACs, the formulation comprising a) AACs wherein the AACs comprise at least one antigen and an adjuvant, and b) a cryopreservation medium.

In some embodiments, the formulation comprises about $1\times10^{7}$ to about $1\times10^{12}$ AACs. In some embodiments, the formulation comprises about $1\times10^{9}$ to about $1\times10^{11}$ AACs in about 9 mL to about 10 mL. In some embodiments, the formulation comprises about any one of $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs in about 9 mL to about 10 mL. In some embodiments, the formulation comprises any one of about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$, about $0.5\times10^{11}$ to about $1.0\times10^{11}$, about $1.0\times10^{11}$ to about $0.5\times10^{12}$ AACs in about 9 mL to about 10 mL. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ AACs in about 9 mL to about 10 mL. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ AACs in about 9.5 mL. In some embodiments, the formulation comprises about $7\times10^{9}$ AACs in about 9 mL to about 10 mL. In some embodiments, the formulation comprises about $7\times10^{9}$ AACs in about 9.5 mL. In some embodiments, the formulation comprises about $6.65\times10^{9}$ AACs in about 9.5 mL. In some embodiments, the formulation comprises about $0.7\times10^{9}$ AACs/mL post-thawing. In some embodiments, the formulation comprises about $0.7\times10^{9}$ AACs/mL post-thawing as measured by Coulter counter. An expected concentration post-thaw of $1.0\times10^{9}$ AAC/mL as measured by a flow cytometry method is approximately equivalent to $7.0\times10^{8}$ AAC/mL post-thaw as measured by a Coulter-based cell counter method based on the negative bias of the Coulter-based counter method due to a lower sensitivity. In some embodiments, the formulation comprises about $1\times10^{7}$ to about $1\times10^{12}$ AACs. In some embodiments, the formulation comprises about $1\times10^{9}$ to about $1\times10^{11}$ AACs. In some embodiments, the formulation comprises about any one of $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs. In some embodiments, the formulation comprises any one of about, about $0.5\times10^{7}$ to about $1.0\times10^{7}$, about $1.0\times10^{7}$ to about $0.5\times10^{8}$ AACs, about $0.5\times10^{8}$ to about $1.0\times10^{8}$, about $1.0\times10^{8}$ to about $0.5\times10^{9}$ AACs, about $0.5\times10^{9}$ to about $1.0\times10^{9}$, about $1.0\times10^{9}$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$, about $1.0\times10^{11}$ to about $0.5\times10^{12}$ AACs. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ AACs. In some embodiments, the formulation comprises about $7\times10^{9}$ AACs. In some embodiments, the formulation comprises about $6.65\times10^{9}$ AACs.

In some embodiments, the volume of the formulation is about 2 mL to about 50 mL. In some embodiments, the volume of the formulation is about 5 mL to about 20 mL. In some embodiments, the volume of the formulation is about any one of 1, 2, 3, 4, 5, 6, 7, 8, 9, 9.5, 10, 10.5, 11, 12, 13, 14, 15, 16, 17, 18, 19, 20, 25, 30, 35, 40, 45, 50 or more mL. In some embodiments, the volume of the formulation is any one of about 1 to about 2, about 2 to about 3, about 3 to about 4, about 4 to about 5, about 5 to about 6, about 6 to about 7, about 7 to about 8, about 8 to about 9, or about 9 to about 10, about 10 to about 11, about 11 to about 12, about 12 to about 13, about 13 to about 14, about 14 to about 15, about 15 to about 16, about 16 to about 17, about 17 to about 18, about 18 to about 19, or about 19 to about 20 mL. In some embodiments, the volume of the formulation is about 9.5 mL.

In some embodiments, the formulation comprises about $1\times10^6$ to about $1\times10^{11}$ AACs/mL. In some embodiments, the formulation comprises about $1\times10^7$ to about $1\times10^{10}$ AACs/mL. In some embodiments, the formulation comprises about any one of $0.5\times10^6$, $0.7\times10^6$, $1.0\times10^6$, $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, and $1.0\times10^{11}$ AACs/mL. In some embodiments, the formulation comprises any one of about, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$ AACs/mL. In some embodiments, the formulation comprises about any one of $1\times10^8$, $2\times10^8$, $3\times10^8$, $4\times10^8$, $5\times10^8$, $6\times10^8$, $7\times10^8$, $8\times10^8$, $9\times10^8$, and $1\times10^9$ AACs/mL. In some embodiments, the formulation comprises about $7\times10^8$ AACs/mL. In some embodiments, the formulation comprises about $6.65\times10^8$ AACs/mL.

In some embodiments, the formulation is sterile. In some embodiments, the formulation comprises less than about 2 EU/mL endotoxin. In some embodiments, the formulation comprises less than any one of about 1, 2, 3, 4, 5, 6, 7, 8, 9, or 10 EU/mL endotoxin. In some embodiments, the formulation is free of mycoplasma.

Formulations of AACs in Cryopreservation Media

In some embodiments according to any one of the methods described herein, the composition of AACs further comprises an agent that enhances the function of the AACs as compared to a corresponding composition of AACs that does not comprise the agent. In some embodiments, the composition of AACs further comprises an agent that enhances the function of the AAC upon freeze-thaw cycle as compared to a corresponding composition of AAC that does not comprise the agent. In some embodiments, the agent is a cryopreservation agent and/or a hypothermic preservation agent. In some embodiments, the cryopreservation agent nor the hypothermic preservation agent prevents more than 10% or 20% of cell death in a composition of AAC comprising the agent compared to a corresponding composition of AAC that does not comprise the agent before any freeze-thaw cycles. In some embodiments, freeze-thaw cycles of compositions of AACs comprising the cryopreservation agent and/or the hypothermic preservation agent causes not more than 10%, 20%, 30%, 40%, or 50% loss in function when compared to a corresponding composition of AACs before the freeze-thaw cycles. In some embodiments, freeze-thaw cycles of AAC compositions comprising the cryopreservation agent and/or the hypothermic preservation agent causes 10%, 20%, 30%, 40%, or 50% less loss of function when compared to freeze-thaw cycles of a corresponding composition of AACs without the cryopreservation agent and the hypothermic preservation agent. In some embodiments, the function or functionality of the AAC composition comprising at least one antigen is measured by the percentage of the AACs that are positive for annexin V staining. In some embodiments, the function or functionality of the AAC composition is measured by the percentage of the AACs that are positive for annexin V staining. In some embodiments, the function or functionality of the AAC composition is measured by the percentage of the AACs that are positive for CD235a staining. In some embodiments, the function or functionality of the AACs composition is measured by the percentage of the anucleate cell-derived vesicles that are positive CD235a and annexin V staining. In some embodiments, at least about 70%, about 80%, or about 90% of the AAC are functional after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is one or more of mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of Mg2+, Zn2+ or Ca2+. In some embodiments, the agent is one or more of: sodium pyruvate, adenine, trehalose, dextrose, mannose, sucrose, human serum albumin (HSA), dimethyl sulfoxide (DMSO), HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CSS, Cryostor® CS10, Cryostor® CS15, HEPES, glycerol, glutathione, HypoThermosol®.

In some embodiments according to any one of the methods described herein, the process further comprises a step of incubating the composition of anucleate cells with an agent that enhances the function of the anucleate cells compared to corresponding anucleate cells prepared without the further incubation step.

In some embodiments, the formulation comprises a cryopreservation medium. In some embodiments, the formulation comprises about $1\times10^9$ to about $1\times10^{11}$ AACs in about 9 mL to about 10 mL cryopreservation medium. In some embodiments, the formulation comprises about any one of $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs in about 9 mL to about 10 mL cryopreservation medium. In some embodiments, the formulation comprises any one of about $0.5\times10^7$ to about $1.0\times10^7$, about $1.0\times10^7$ to about $0.5\times10^8$ AACs, about $0.5\times10^8$ to about $1.0\times10^8$, about $1.0\times10^8$ to about $0.5\times10^9$ AACs, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ AACs in about 9 mL to about 10 mL cryopreservation medium. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs in about 9 mL to about 10 mL cryopreservation medium. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs in about 9.5 mL cryopreservation medium. In some embodiments, the formulation comprises about $7\times10^9$ AACs in about 9 mL to about 10 mL cryopreservation medium. In some embodiments, the formulation comprises about $7\times10^9$ AACs in about 9.5 mL cryopreservation medium. In some embodiments, the formulation comprises about $6.65\times10^9$ AACs in about 9.5 mL cryopreservation medium. In some embodiments, the formulation comprising AACs comprise about any one of $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs in a cryopreservation medium. In some embodiments, the formulation comprises any one of about, about $0.5\times10^7$ to about $1.0\times10^7$, about $1.0\times10^7$ to about $0.5\times10^8$ AACs, about $0.5\times10^8$ to about $1.0\times10^8$, about $1.0\times10^8$ to about $0.5\times10^9$ AACs, about $0.5\times10^9$ to about $1.0\times10^9$, about $1.0\times10^9$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ AACs in a cryopreservation medium. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs in a cryopreservation medium. In some embodiments, the formulation comprises about $7\times10^9$ AACs in a cryopreservation medium. In some embodiments, the formulation comprises about $6.65\times10^9$ AACs in a cryopreservation medium. In some embodiments, the formulation comprises about $0.7\times10^9$ AACs/mL in cryopreservation medium post-thawing. In some embodiments, the formulation comprises about $0.7\times10^9$ AACs/mL in cryopreservation medium post-thawing as measured by Coulter counter. In some embodiments, the cryopreservation medium comprises CryoStor® CS2. In some embodiments, the cryopreservation medium is CryoStor® CS2.

In some embodiments, the composition comprising AACs comprise about $7\times10^9$ AACs in about 9 mL to about 10 mL of CryoStor® CS2. In some embodiments, the composition comprising AACs comprise about $7\times10^9$ AACs in about 9.5 mL of CryoStor® CS2. In some embodiments, the formulation comprises about $6.65\times10^9$ AACs in about 9.5 mL of CryoStor® CS2.

In some embodiments, the AACs in the formulation maintain equal to or greater than about 50% functionality up to 1, 2, 3, 4, 5 freeze-thaw cycles. In some embodiments, the formulation maintain equal to or greater than about 50%, 60%, 70%, 80%, 90%, 95%, or 99% functionality up to 1, 2, 3, 4, 5 freeze-thaw cycles. In some embodiments, the AACs in the formulation maintain equal to or greater than about 70% functionality following storage for at least 12 months at temperatures at or below −140 °C. In some embodiments, the formulation maintain equal to or greater than about 50%, 60%, 70%, 80%, 90%, 95%, or 99% functionality following storage for at least 12 months at temperatures at or below −140 °C. In some embodiments, the formulation maintain equal to or greater than about 70% functionality following storage for at least 6, 9, 12, 15, 18, 24, 30, or 36 months at temperatures at or below −140 °C. In some embodiments, the formulation maintain equal to or greater than about 70% functionality following storage for at least 12 months at temperatures at or below −100 °C, −110 °C, −120 °C, −130 °C, −140 °C, −150 °C, −160 °C, −170 °C, −180 °C, −190 °C, or −200 °C.

In some embodiments, the AACs in the formulation maintain equal to or greater than about 50% positive staining for annexin up to 1, 2, 3, 4, 5 freeze-thaw cycles. In some embodiments, the formulation maintain equal to or greater than about 50%, 60%, 70%, 80%, 90%, 95%, or 99% positive staining for annexin up to 1, 2, 3, 4, 5 freeze-thaw cycles. In some embodiments, the AACs in the formulation maintain equal to or greater than about 70% positive staining for annexin following storage for at least 12 months at temperatures at or below −140 °C In some embodiments, the formulation maintain equal to or greater than about 50%, 60%, 70%, 80%, 90%, 95%, or 99% positive staining for annexin following storage for at least 12 months at temperatures at or below −140 °C. In some embodiments, the formulation maintain equal to or greater than about 70% positive staining for annexin following storage for at least 6, 9, 12, 15, 18, 24, 30, or 36 months at temperatures at or below −140 °C. In some embodiments, the formulation maintain equal to or greater than about 70% positive staining for annexin following storage for at least 12 months at temperatures at or below −100 °C, −110 °C, −120 °C, −130 °C, −140 °C, −150 °C, −160 °C, −170 °C, −180 °C, −190 °C, or −200 °C In some embodiments, the AACs in the formulation maintain equal to or greater than about 50% positive staining for annexin V and/or CD235a up to 1, 2, 3, 4, 5 freeze-thaw cycles. In some embodiments, the formulation maintain equal to or greater than about 50%, 60%, 70%, 80%, 90%, 95%, or 99% positive staining for annexin V and/or CD235a up to 1, 2, 3, 4, 5 freeze-thaw cycles. In some embodiments, the AACs in the formulation maintain equal to or greater than about 70% positive staining for annexin V and/or CD235a following storage for at least 12 months at temperatures at or below −140 °C. In some embodiments, the formulation maintain equal to or greater than about 50%, 60%, 70%, 80%, 90%, 95%, or 99% positive staining for annexin V and/or CD235a following storage for at least 12 months at temperatures at or below −140 °C. In some embodiments, the formulation maintain equal to or greater than about 70% positive staining for annexin V and/or CD235a following storage for at least 6, 9, 12, 15, 18, 24, 30, or 36 months at temperatures at or below −140 °C. In some embodiments, the formulation maintain equal to or greater than about 70% positive staining for annexin V and/or CD235a following storage for at least 12 months at temperatures at or below −100 °C, −110 °C, −120 °C, −130 °C, −140 °C, −150 °C, −160 °C, −170 °C, −180 °C, −190 °C, or −200 °C.

In some embodiments, the formulation comprising AACs comprise about any one of $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ functional AACs. In some embodiments, the formulation comprises any one of about, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10$, about $0.5\times10^9$ to about $1.0\times10^9$, about $1.0\times10^9$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$, about $1.0\times10^{11}$ to about $0.5\times10^{12}$ functional AACs. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ functional AACs. In some embodiments, the formulation comprises about $7\times10^9$ functional AACs. In some embodiments, the formulation comprises about $1\times10^9$ to about $1\times10^{10}$ functional AACs.

In some embodiments, the formulation comprises about $1\times10^{6}$ to about $1\times10^{11}$ functional AACs/mL. In some embodiments, the formulation comprises about $1\times10^{7}$ to about $1\times10^{10}$ functional AACs/mL. In some embodiments, the formulation comprises about any one of $0.5\times10^{6}$, $0.7\times10^{6}$, $1.0\times10^{6}$, $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, and $1.0\times10^{11}$ functional AACs/mL. In some embodiments, the formulation comprises any one of about, about $0.5\times10^{6}$ to about $1.0\times10^{6}$, about $1.0\times10^{6}$ to about $0.5\times10^{7}$, about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$ functional AACs/mL. In some embodiments, the formulation comprises about any one of $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, and $1\times10^{9}$ functional AACs/mL. In some embodiments, the formulation comprises about $7\times10^{8}$ functional AACs/mL. In some embodiments, the formulation comprises about $1\times10^{8}$ to about $1\times10^{9}$ functional AACs/mL.

In some embodiments, the formulation comprising AACs comprise about any one of $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ functional AACs post-thawing. In some embodiments, the formulation comprises any one of about $0.5\times10^{7}$ to about $1.0\times10^{7}$, about $1.0\times10^{7}$ to about $0.5\times10^{8}$ AACs, about $0.5\times10^{8}$ to about $1.0\times10^{8}$, about $1.0\times10^{8}$ to about $0.5\times10^{9}$ AACs, about $0.5\times10^{9}$ to about $1.0\times10^{9}$, about $1.0\times10^{9}$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ functional AACs post-thawing. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ functional AACs post-thawing. In some embodiments, the formulation comprises about $7\times10^{9}$ functional AACs post-thawing. In some embodiments, the formulation comprises about $1\times10^{9}$ to about $1\times10^{10}$ functional AACs post-thawing.

In some embodiments, the formulation comprises about $1\times10^{6}$ to about $1\times10^{11}$ functional AACs/mL post-thawing. In some embodiments, the formulation comprises about $1\times10^{7}$ to about $1\times10^{10}$ functional AACs/mL post-thawing. In some embodiments, the formulation comprises about any one of $0.5\times10^{6}$, $0.7\times10^{6}$, $1.0\times10^{6}$, $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, and $1.0\times10^{11}$ functional AACs/mL post-thawing. In some embodiments, the formulation comprises any one of about, about $0.5\times10^{6}$ to about $1.0\times10^{6}$, about $1.0\times10^{6}$ to about $0.5\times10^{7}$, about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$ functional AACs/mL post-thawing. In some embodiments, the formulation comprises about any one of $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, and $1\times10^{9}$ functional AACs/mL post-thawing. In some embodiments, the formulation comprises about $7\times10^{8}$ functional AACs/mL post-thawing. In some embodiments, the formulation comprises about $1\times10^{8}$ to about $1\times10^{9}$ functional AACs/mL post-thawing.

In some embodiments, the cryopreservation medium comprises dimethylsulfoxide (DMSO). In some embodiments, the cryopreservation medium comprises about 0.5% to about 25% DMSO. In some embodiments, the cryopreservation medium comprises about 0.5% to about 5% DMSO. In some embodiments, the cryopreservation medium comprises about any one of 0.5%, 1%, 1.5%, 2%, 2.5%, 3%, 3.5%, 4%, 4.5%, 5%, 10%, 15%, 20% and 25% DMSO. In some embodiments, the cryopreservation medium comprises any one of about 0.5% to about 5%, about 5% to about 10%, about 10% to about 20% DMSO. In some embodiments, the cryopreservation medium comprises about 2% DMSO.

In some embodiments, the pH of the formulation is about 5.0 to about 9.5. In some embodiments, the pH of the formulation is about 6.0 to about 8.5. In some embodiments, the pH of the formulation is about 7.6. In some embodiments, the pH of the formulation is any one of about 5, 5.5, 6, 6.5, 7, 7.5, 8, 8.5, 9 or 10. In some embodiments, the pH of the formulation is any one of about 7, 7.1, 7.2, 7.3, 7.4, 7.5, 7.6, 7.7, 7.8, 7.9, or 8.0. In some embodiments, the pH of the formulation is any one of about 5 to about 6, about 6 to about 7, about 7 to about 8, about 8 to about 9, or about 9 to about 10. In some embodiments, the pH of the formulation is any one of about 7 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.8 to about 7.9, or about 7.9 to about 8.0.

In some aspects, there is provided a pharmaceutical formulation of AACs, the formulation comprising about $0.5\times10^{9}$ AACs to about $1\times10^{10}$ AACs in cryopreservation medium, wherein AACs comprise at least one antigen and an adjuvant, wherein the pH of the formulation is about pH 6.0 to about pH 8.5. In some embodiments, there is provided a pharmaceutical formulation of AACs, the formulation comprising about $0.5\times10^{9}$ AACs to about $1\times10^{10}$ AACs in a cryopreservation medium, wherein AACs comprise at least one antigen and an adjuvant, wherein the pH of the formulation is about pH 7.6. In some embodiments, the formulation comprises about $0.7\times10^{9}$ AACs/mL post-thawing. In some embodiments, the formulation comprises about $0.7\times10^{9}$ AACs/mL post-thawing as measured by Coulter counter.

In some embodiments, the formulation comprises about $1\times10^{6}$ to about $1\times10^{11}$ AACs/mL prior to freezing. In some embodiments, the formulation comprises about $1\times10^{7}$ to about $1\times10^{10}$ AACs/mL prior to freezing. In some embodiments, the formulation comprises about any one of $0.5\times10^{6}$, $0.7\times10^{6}$, $1.0\times10^{6}$, $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, and $1.0\times10^{11}$ AACs/mL prior to freezing. In some embodiments, the formulation comprises any one of about, about $0.5\times10^{6}$ to about $1.0\times10^{6}$, about $1.0\times10^{6}$ to about $0.5\times10^{7}$, about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$ AACs/mL prior to freezing. In some embodiments, the formulation comprises about any one of $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, and $1\times10^{9}$ AACs/mL prior to freezing. In some embodiments, the formulation comprises about $7\times10^{8}$ AACs/mL prior to freezing. In some embodiments, the formulation comprises about $6.65\times10^{8}$ AACs/mL prior to freezing. In some embodiments, the concentration of AACs in the formulation is measured by Coulter counter.

In some embodiments, the formulation comprising AACs comprise about any one of $0.5\times10^{7}$, $0.7\times10^{7}$, $1.0\times10^{7}$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs prior to freezing. In some embodiments, the formulation comprises any one of about, about $0.5\times10^7$ to about $1.0\times10^7$, about $1.0\times10^7$ to about $0.5\times10^8$ AACs, about $0.5\times10^8$ to about $1.0\times10^8$, about $1.0\times10^8$ to about $0.5\times10^9$ AACs, about $0.5\times10^9$ to about $1.0\times10^9$, about $1.0\times10^9$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ AACs prior to freezing. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs prior to freezing. In some embodiments, the formulation comprises about $7\times10^9$ AACs prior to freezing. In some embodiments, the formulation comprises about $6.65\times10^9$ AACs prior to freezing.

In some embodiments, the formulation comprises about $1\times10^6$ to about $1\times10^{11}$ AACs/mL post-thawing. In some embodiments, the formulation comprises about $1\times10^7$ to about $1\times10^{10}$ AACs/mL post-thawing. In some embodiments, the formulation comprises about any one of $0.5\times10^6$, $0.7\times10^6$, $1.0\times10^6$, $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, and $1.0\times10^{11}$ AACs/mL post-thawing. In some embodiments, the formulation comprises any one of about, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$ AACs/mL post-thawing. In some embodiments, the formulation comprises about any one of $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, and $5\times10^9$ AACs/mL post-thawing. In some embodiments, the formulation comprises about $7\times10^8$ AACs/mL post-thawing. In some embodiments, the formulation comprises about $6.65\times10^8$ AACs/mL post-thawing. In some embodiments, the formulation comprises about $1\times10^9$ AACs/mL post-thawing.

In some embodiments, the formulation comprises about $1\times10^6$ to about $1\times10^{11}$ AACs/mL post-thawing as measured by Coulter counter. In some embodiments, the formulation comprises about $1\times10^7$ to about $1\times10^{10}$ AACs/mL post-thawing as measured by Coulter counter. In some embodiments, the formulation comprises about any one of $0.5\times10^6$, $0.7\times10^6$, $1.0\times10^6$, $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, and $1.0\times10^{11}$ AACs/mL post-thawing as measured by Coulter counter. In some embodiments, the formulation comprises any one of about, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$ AACs/mL post-thawing as measured by Coulter counter. In some embodiments, the formulation comprises about any one of $1\times10^8$, $2\times10^8$, $3\times10^8$, $4\times10^8$, $5\times10^8$, $6\times10^8$, $7\times10^8$, $8\times10^8$, $9\times10^8$, and $1\times10^9$ AACs/mL post-thawing as measured by Coulter counter. In some embodiments, the formulation comprises about $7\times10^8$ AACs/mL post-thawing as measured by Coulter counter. In some embodiments, the formulation comprises about $6.65\times10^8$ AACs/mL post-thawing as measured by Coulter counter.

In some embodiments, the formulation comprises about $1\times10^6$ to about $1\times10^{11}$ AACs/mL post-thawing as measured by flow cytometry. In some embodiments, the formulation comprises about $1\times10^7$ to about $1\times10^{10}$ AACs/mL post-thawing as measured by flow cytometry. In some embodiments, the formulation comprises about any one of $0.5\times10^6$, $1.0\times10^6$, $0.5\times10^7$, $1.0\times10^7$, $0.5\times10^8$, $1.0\times10^8$, $0.5\times10^9$, $1.0\times10^9$, $0.5\times10^{10}$, $1.0\times10^{10}$, $0.5\times10^{11}$, and $1.0\times10^{11}$ AACs/mL post-thawing as measured by flow cytometry. In some embodiments, the formulation comprises any one of about, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$ AACs/mL post-thawing as measured by flow cytometry. In some embodiments, the formulation comprises about any one of $5\times10^8$, $6\times10^8$, $7\times10^8$, $8\times10^8$, $9\times10^8$, $1\times10^9$, $2\times10^9$, $3\times10^9$, $4\times10^9$, $5\times10^9$ AACs/mL post-thawing as measured by flow cytometry. In some embodiments, the formulation comprises about $1\times10^9$ AACs/mL post-thawing as measured by flow cytometry.

In some embodiments, the formulation comprising AACs comprise about any one of $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$ $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs post-thawing. In some embodiments, the formulation comprises any one of about, about $0.5\times10^7$ to about $1.0\times10^7$, about $1.0\times10^7$ to about $0.5\times10^8$ AACs, about $0.5\times10^8$ to about $1.0\times10^8$, about $1.0\times10^8$ to about $0.5\times10^9$ AACs, about $0.5\times10^9$ to about $1.0\times10^9$, about $1.0\times10^9$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ AACs post-thawing. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs post-thawing. In some embodiments, the formulation comprises about $9\times10^9$ AACs post-thawing. In some embodiments, the formulation comprises about $7\times10^9$ AACs post-thawing. In some embodiments, the formulation comprises about $6.65\times10^9$ AACs post-thawing.

In some embodiments according to any of the formulations described herein, the AACs are in about 2 mL to about 50 mL of cryopreservation medium. In some embodiments, the AACs are in about 5 mL to about 20 mL of cryopreservation medium. In some embodiments, the AACs are in about any one of 1, 2, 3, 4, 5, 6, 7, 8, 9, 9.5, 10, 10.5, 11, 12, 13, 14, 15, 16, 17, 18, 19, 20, 25, 30, 35, 40, 45, 50 or more mL of cryopreservation medium. In some embodiments, the AACs are in any one of about 1 to about 2, about 2 to about 3, about 3 to about 4, about 4 to about 5, about 5 to about 6, about 6 to about 7, about 7 to about 8, about 8 to about 9, or about 9 to about 10, about 10 to about 11, about 11 to about 12, about 12 to about 13, about 13 to about 14, about 14 to about 15, about 15 to about 16, about 16 to about 17, about 17 to about 18, about 18 to about 19, or about 19 to about 20 mL of cryopreservation medium. In some embodiments, the AACs are in about 9.5 mL of cryopreservation medium.

In some aspects, provided is a pharmaceutical formulation of AACs, the formulation comprising about $7\times10^9$ AACs in about 9.5 mL of cryopreservation medium, wherein AACs comprise at least one antigen and an adjuvant, and wherein the pH of the formulation is about pH 7.6. In some embodiments, the cryopreservation medium is CryoStor® CS2.

In some embodiments, the formulation is sterile. In some embodiments, the formulation comprises less than about 2 EU/mL endotoxin. In some embodiments, the formulation comprises less than any one of about 1, 2, 3, 4, 5, 6, 7, 8, 9, or 10 EU/mL endotoxin. In some embodiments, the formulation is free of mycoplasma.

Vials Comprising Pharmaceutical Formulation

In some embodiments, there is provided a vial comprising any one of the pharmaceutical formulations described herein.

In some aspects, there is provided a vial comprising a pharmaceutical formulation, wherein the pharmaceutical formulation comprises AACs, wherein the formulation comprising about $1\times10^9$ AACs to about $1\times10^{10}$ AACs in cryopreservation medium, wherein AACs comprise at least one antigen and an adjuvant, wherein the pH of the formulation is about pH 6.0 to about pH 8.5. In some embodiments, there is provided a pharmaceutical formulation of AACs, the formulation comprising about $1\times10^9$ AACs to about $1\times10^{10}$ AACs in a cryopreservation medium, wherein AACs comprise at least one antigen and an adjuvant, wherein the pH of the formulation is about pH 7.6.

In some embodiments according to any of the vials described herein, the AACs are in about 2 mL to about 50 mL of cryopreservation medium. In some embodiments, the AACs are in about 5 mL to about 20 mL of cryopreservation medium. In some embodiments, the AACs are in about any one of 1, 2, 3, 4, 5, 6, 7, 8, 9, 9.5, 10, 10.5, 11, 12, 13, 14, 15, 16, 17, 18, 19, 20, 25, 30, 35, 40, 45, 50 or more mL of cryopreservation medium. In some embodiments, the AACs are in any one of about 1 to about 2, about 2 to about 3, about 3 to about 4, about 4 to about 5, about 5 to about 6, about 6 to about 7, about 7 to about 8, about 8 to about 9, or about 9 to about 10, about 10 to about 11, about 11 to about 12, about 12 to about 13, about 13 to about 14, about 14 to about 15, about 15 to about 16, about 16 to about 17, about 17 to about 18, about 18 to about 19, or about 19 to about 20 mL of cryopreservation medium.

In some embodiments, the formulation comprises about $1\times10^6$ to about $1\times10^{11}$ AACs/mL. In some embodiments, the formulation comprises about $1\times10^7$ to about $1\times10^{10}$ AACs/mL. In some embodiments, the formulation comprises about any one of $0.5\times10^6$, $0.7\times10^6$, $1.0\times10^6$, $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, and $1.0\times10^{11}$ AACs/mL. In some embodiments, the formulation comprises any one of about, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$ AACs/mL. In some embodiments, the formulation comprises about any one of $1\times10^8$, $2\times10^8$, $3\times10^8$, $4\times10^8$, $5\times10^8$, $6\times10^8$, $7\times10^8$, $8\times10^8$, $9\times10^8$, and $1\times10^9$ AACs/mL. In some embodiments, the formulation comprises about $7\times10^8$ AACs/mL. In some embodiments, the formulation comprises about $6.65\times10^8$ AACs/mL. In some embodiments, the cryopreservation medium is CryoStor® CS2. In some embodiments, the cryopreservation medium comprises DMSO. In some embodiments, the cryopreservation medium comprises about 0.5% to about 25% DMSO. In some embodiments, the cryopreservation medium comprises about 0.5% to about 5% DMSO. In some embodiments, the cryopreservation medium comprises about any one of 0.5%, 1%, 1.5%, 2%, 2.5%, 3%, 3.5%, 4%, 4.5%, 5%, 10%, 15%, 20% and 25% DMSO. In some embodiments, the cryopreservation medium comprises any one of about 0.5% to about 5%, about 5% to about 10%, about 10% to about 20% DMSO. In some embodiments, the cryopreservation medium comprises about 2% DMSO.

In some embodiments, the pH of the formulation is about 5.0 to about 9.5. In some embodiments, the pH of the formulation is about 6.0 to about 8.5. In some embodiments, the pH of the formulation is about 7.6. In some embodiments, the pH of the formulation is any one of about 5, 5.5, 6, 6.5, 7, 7.5, 8, 8.5, 9 or 10. In some embodiments, the pH of the formulation is any one of about 7, 7.1, 7.2, 7.3, 7.4, 7.5, 7.6, 7.7, 7.8, 7.9, or 8.0. In some embodiments, the pH of the formulation is any one of about 5 to about 6, about 6 to about 7, about 7 to about 8, about 8 to about 9, or about 9 to about 10. In some embodiments, the pH of the formulation is any one of about 7 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.8 to about 7.9, or about 7.9 to about 8.0.

In some embodiments, the formulation comprises about $1\times10^9$ to about $1\times10^{11}$ AACs in about 9 mL to about 10 mL. In some embodiments, the formulation comprises about any one of $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs in about 9 mL to about 10 mL. In some embodiments, the formulation comprises any one of about $0.5\times10^7$ to about $1.0\times10^7$, about $1.0\times10^7$ to about $0.5\times10^8$ AACs, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$, about $0.5\times10^{11}$ to about $1.0\times10^{11}$, about $1.0\times10^{11}$ to about $0.5\times10^{12}$ AACs in about 9 mL to about 10 mL. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs in about 9 mL to about 10 mL. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs in about 9.5 mL. In some embodiments, the formulation comprises about $7\times10^9$ AACs in about 9 mL to about 10 mL. In some embodiments, the formulation comprises about $7\times10^9$ AACs in about 9.5 mL. In some embodiments, the formulation comprising AACs comprise about any one of $0.5\times10^7$, $0.7\times10^7$, $1.0\times10^7$, $0.5\times10^8$, $0.7\times10^8$, $1.0\times10^8$, $0.5\times10^9$, $0.7\times10^9$, $1.0\times10^9$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs. In some embodiments, the formulation comprises any one of about, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, about $1.0\times10^9$ to about $0.5\times10^{10}$, about $0.5\times10^{10}$ to about $1.0\times10^{10}$, about $1.0\times10^{10}$ to about $0.5\times10^{11}$, about $0.5\times10^{11}$ to about $1.0\times10^{11}$, about $1.0\times10^{11}$ to about $0.5\times10^{12}$ AACs. In some embodiments, the formulation comprises about any one of $1\times10^9$, $2\times10^9$, $3\times10^9$, $4\times10^9$, $5\times10^9$, $6\times10^9$, $7\times10^9$, $8\times10^9$, $9\times10^9$, and $1\times10^{10}$ AACs. In some embodiments, the formulation comprises about $7\times10^9$ AACs in a cryopreservation medium. In some embodiments, the formulation comprises about $0.7\times10^9$ AACs/mL in cryopreservation medium post-thawing. In some embodiments, the formulation comprises about $0.7\times10^9$ AACs/mL in cryopreservation medium post-thawing as measured by Coulter counter. In some embodiments, the cryopreservation medium comprises CryoStor® CS2. In some embodiments, the cryopreservation medium is CryoStor® CS2. In some embodiments, the formulation comprises about $1\times10^{6}$ to about $1\times10^{11}$ AACs/mL post-thawing. In some embodiments, the formulation comprises about $1\times10^{7}$ to about $1\times10^{10}$ AACs/mL post-thawing. In some embodiments, the formulation comprises about any one of $0.5\times10^{6}$, $0.7\times10^{6}$, $1.0\times10^{6}$, $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, 0.5x1010, $0.7\times10^{10}$, $1.0\times10^{10}$, $0.5\times10^{11}$, $0.7\times10^{11}$, and $1.0\times10^{11}$ AACs/mL post-thawing. In some embodiments, the formulation comprises any one of about, about $0.5\times10^{6}$ to about $1.0\times10^{6}$, about $1.0\times10^{6}$ to about $0.5\times10^{7}$, about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$ AACs/mL post-thawing. In some embodiments, the formulation comprises about any one of $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, and $1\times10^{9}$ AACs/mL post-thawing. In some embodiments, the formulation comprises about $7\times10^{8}$ AACs/mL post-thawing. In some embodiments, the formulation comprises about $6.65\times10^{8}$ AACs/mL post-thawing. In some embodiments, the formulation comprises about $1\times10^{9}$ AACs/mL post-thawing.

In some embodiments, the formulation comprises about $1\times10^{6}$ to about $1\times10^{11}$ AACs/mL post-thawing as measured by Coulter counter. In some embodiments, the formulation comprises about $1\times10^{7}$ to about $1\times10^{10}$ AACs/mL post-thawing as measured by Coulter counter. In some embodiments, the formulation comprises about any one of $0.5\times10^{6}$, $0.7\times10^{6}$, $1.0\times10^{6}$, $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, and $1.0\times10^{11}$ AACs/mL post-thawing as measured by Coulter counter. In some embodiments, the formulation comprises any one of about, about $0.5\times10^{6}$ to about $1.0\times10^{6}$, about $1.0\times10^{6}$ to about $0.5\times10^{7}$, about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$ AACs/mL post-thawing as measured by Coulter counter. In some embodiments, the formulation comprises about any one of $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, and $1\times10^{9}$ AACs/mL post-thawing as measured by Coulter counter. In some embodiments, the formulation comprises about $7\times10^{8}$ AACs/mL post-thawing as measured by Coulter counter. In some embodiments, the formulation comprises about $6.65\times10^{8}$ AACs/mL post-thawing as measured by Coulter counter.

In some embodiments, the formulation comprises about $1\times10^{6}$ to about $1\times10^{11}$ AACs/mL post-thawing as measured by flow cytometry. In some embodiments, the formulation comprises about $1\times10^{7}$ to about $1\times10^{10}$ AACs/mL post-thawing as measured by flow cytometry. In some embodiments, the formulation comprises about any one of $0.5\times10^{6}$, $1.0\times10^{6}$, $0.5\times10^{7}$, $1.0\times10^{7}$, $0.5\times10^{8}$, $1.0\times10^{8}$, $0.5\times10^{9}$, $1.0\times10^{9}$, $0.5\times10^{10}$, $1.0\times10^{10}$, $0.5\times10^{11}$, and $1.0\times10^{11}$ AACs/mL post-thawing as measured by flow cytometry. In some embodiments, the formulation comprises any one of about, about $0.5\times10^{6}$ to about $1.0\times10^{6}$, about $1.0\times10^{6}$ to about $0.5\times10^{7}$, about $0.5\times10^{7}$ to about $1.0\times10^{7}$, about $1.0\times10^{7}$ to about $0.5\times10^{8}$, about $0.5\times10^{8}$ to about $1.0\times10^{8}$, about $1.0\times10^{8}$ to about $0.5\times10^{9}$, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$ AACs/mL post-thawing as measured by flow cytometry. In some embodiments, the formulation comprises about any one of $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$ AACs/mL post-thawing as measured by flow cytometry. In some embodiments, the formulation comprises about $1\times10^{9}$ AACs/mL post-thawing as measured by flow cytometry.

In some embodiments, the formulation comprising AACs comprise about any one of $0.5\times10^{7}$, $0.7\times10^{7}$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$ $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs post-thawing. In some embodiments, the formulation comprises any one of about, about $0.5\times10^{7}$ to about $1.0\times10^{7}$, about $1.0\times10^{7}$ to about $0.5\times10^{8}$ AACs, about $0.5\times10^{8}$ to about $1.0\times10^{8}$, about $1.0\times10^{8}$ to about $0.5\times10^{9}$ AACs, about $0.5\times10^{9}$ to about $1.0\times10^{9}$, about $1.0\times10^{9}$ to about $0.5\times10^{10}$ AACs, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ AACs post-thawing. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ AACs post-thawing. In some embodiments, the formulation comprises about $9\times10^{9}$ AACs post-thawing. In some embodiments, the formulation comprises about $7\times10^{9}$ AACs post-thawing. In some embodiments, the formulation comprises about $6.65\times10^{9}$ AACs post-thawing.

In some aspects, provided is a pharmaceutical formulation of activated AACs, the formulation comprising about $7\times10^{9}$ AACs in about 9.5 mL of cryopreservation medium, wherein AACs comprise at least one antigen and an adjuvant, and wherein the pH of the formulation is about pH 7.6. In some embodiments, the cryopreservation medium is CryoStor® CS2.

In some embodiments, the formulation is sterile. In some embodiments, the formulation comprises less than about 2 EU/mL endotoxin. In some embodiments, the formulation comprises less than any one of about 1, 2, 3, 4, 5, 6, 7, 8, 9, or 10 EU/mL endotoxin. In some embodiments, the formulation is free of mycoplasma.

Compositions of AACs Comprising Antigens and Adjuvants

In some embodiments, the AACs comprise an antigen and an adjuvant delivered intracellularly. In some embodiments, the AACs comprise an HPV antigen and an adjuvant delivered intracellularly. In some embodiments, the AACs are derived from input anucleate cells. In some embodiments, the AACs are derived from input erythrocytes. In some embodiments, the AACs are derived from input reticulocytes. In some embodiments, the AACs are derived from input red blood cells (RBCs). In some embodiments, the AACs are anucleate cell-derived vesicles comprising the HPV antigen and the adjuvant. In some embodiments, the AACs are RBC-derived vesicles comprising the HPV antigen and the adjuvant.

In some embodiments, the AACs comprising the at least one antigen and the adjuvant are prepared by: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed input anucleate cells; and b) incubating the perturbed input anucleate cells with the at least one antigen and the adjuvant for a sufficient time to allow the at least one antigen and the adjuvant to enter the perturbed input anucleate cells; thereby generating AACs comprising the at least one antigen and the adjuvant.

In some embodiments, the AACs comprising the HPV antigen and the adjuvant are prepared by: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the HPV antigen and the adjuvant to pass through to form perturbed input anucleate cells; and b) incubating the perturbed input anucleate cells with the HPV antigen and the adjuvant for a sufficient time to allow the HPV antigen and the adjuvant to enter the perturbed input anucleate cells; thereby generating AACs comprising the HPV antigen and the adjuvant. In some embodiments, the HPV antigen comprises the amino acid sequence of any one of SEQ ID Nos: 1-4 and 18-25. In some embodiments, the HPV antigen comprises an amino acid sequence with at least 90% identity to any one of SEQ ID Nos: 1-4 and 18-25.

In some embodiments, the anucleate cell is an RBC or a platelet. In some embodiments, the anucleate cell is an erythrocyte or a reticulocyte. In some embodiments, the AAC is an anucleate cell-derived vesicle. In some embodiments, the anucleate cell-derived vesicle is an RBC-derived vesicle or a platelet-derived vesicle. In some embodiments, the anucleate cell-derived vesicle is an erythrocyte-derived vesicle or a reticulocyte-derived vesicle.

In some embodiments, the AACs comprising the at least one antigen and the adjuvant are prepared by: a) passing a cell suspension comprising input red blood cells through a cell-deforming constriction, wherein a diameter of the constriction is a function of a diameter of the input red blood cells in the suspension, thereby causing perturbations of the input red blood cells large enough for the at least one antigen and the adjuvant to pass through to form perturbed input red blood cells; and b) incubating the perturbed input red blood cells with the at least one antigen and the adjuvant for a sufficient time to allow the at least one antigen and the adjuvant to enter the perturbed input red blood cells; thereby generating AACs comprising the at least one antigen and the adjuvant.

In some embodiments, the AACs comprising the HPV antigen and the adjuvant are prepared by: a) passing a cell suspension comprising input red blood cells through a cell-deforming constriction, wherein a diameter of the constriction is a function of a diameter of the input red blood cells in the suspension, thereby causing perturbations of the input red blood cells large enough for the HPV antigen and the adjuvant to pass through to form perturbed input red blood cells; and b) incubating the perturbed input red blood cells with the HPV antigen and the adjuvant for a sufficient time to allow the HPV antigen and the adjuvant to enter the perturbed input red blood cells; thereby generating AACs comprising the HPV antigen and the adjuvant. In some embodiments, the HPV antigen comprises the amino acid sequence of any one of SEQ ID Nos: 1-4, and 18-25. In some embodiments, the HPV antigen comprises an amino acid sequence with at least 90% identity to any one of SEQ ID Nos:1-4, and 18-25.

In some embodiments, the width of the constriction is about 10% to about 99% of the mean diameter of the input anucleate cells (e.g., red blood cells). In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input anucleate cells. In some embodiments, the width of the constriction about 0.25 μm to about 4 μm, about 1 μm to about 4 μm, about 1.2 μm to about 3 μm, about 1.4 μm to about 2.6 μm, about 1.6 μm to about 2.4 μm, or about 1.8 μm to about 2.2 μm. In some embodiments, the width of the constriction is about 2.0 μm. In some embodiments, the width of the constriction is about 2.5 μm. In some embodiments, the width of the constriction is about 3.0 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the cell suspension comprising the input anucleate cells are passed through multiple constrictions wherein the multiple constrictions are arranged in series and/or in parallel.

In some embodiments, the HPV antigen is a pool of multiple polypeptides that elicit a response against the same and or different HPV antigens. In some embodiments, the HPV antigen is a polypeptide comprising one or more antigenic HPV epitope and one or more heterologous peptide sequences. In some embodiments, the HPV antigen complexes with other antigens or with an adjuvant. In some embodiments, the HPV antigen is capable of being processed into an MHC class I-restricted peptide. In some embodiments, the HPV antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

Methods of Generating Pharmaceutical Formulations Comprising AACs Comprising an Antigen and an Adjuvant In some embodiments, the AACs comprised within the pharmaceutical formulations are anucleate cell-derived vesicles. In some embodiments, provided are methods for generating a composition comprising AACs comprising an antigen and an adjuvant, wherein the at least one antigen and adjuvant are delivered to the AACs intracellularly. In some embodiments, provided are methods for generating a composition comprising AACs comprising a HPV antigen and an adjuvant, wherein the HPV antigen and the adjuvant is delivered to the AACs intracellularly.

In some embodiments according to any of the formulations described herein, the AACs comprising at least one antigen and adjuvant are prepared by a process comprising: a) passing a cell suspension comprising a population of input anucleate through a cell-deforming constriction, wherein a diameter of the constriction is a function of a diameter of the input anucleate cells in the suspension, thereby causing perturbations of the input anucleate cells large enough for the at least one antigen and adjuvant to pass through to form perturbed input anucleate cells; and b) incubating the population of perturbed input anucleate cells with the at least one antigen and adjuvant for a sufficient time to allow the at least one antigen to enter the perturbed input anucleate cells, thereby generating the AACs comprising the at least one antigen and adjuvant.

In some embodiments, the AACs comprising the HPV antigen and an adjuvant are prepared by a process comprising: a) passing a cell suspension comprising a population of input anucleate through a cell-deforming constriction, wherein a diameter of the constriction is a function of a diameter of the input anucleate cells in the suspension, thereby causing perturbations of the input anucleate cells large enough for the HPV antigen and the adjuvant to pass through to form perturbed input anucleate cells; and b) incubating the population of perturbed input anucleate cells with the HPV antigen and the adjuvant for a sufficient time to allow the at least one antigen to enter the perturbed input anucleate cells, thereby generating the AACs comprising the HPV antigen and the adjuvant.

In some embodiments, the HPV antigen comprises a peptide derived from HPV E6. In some embodiments, the HPV antigen comprises a peptide derived from HPV E7. In some embodiments, the HPV antigen comprises a peptide derived from HPV E6 and a peptide derived from HPV E7.

In some embodiments, the input anucleate cell is a red blood cell (RBC) or a platelet. In some embodiments, the input anucleate cell is an erythrocyte or a reticulocyte. In some embodiments, the AAC is an anucleate cell-derived vesicle. In some embodiments, the anucleate cell-derived vesicle is a RBC-derived vesicle or a platelet-derived vesicle. In some embodiments, the anucleate cell-derived vesicle is an erythrocyte-derived vesicle or a reticulocyte-derived vesicle. In some embodiments, the input anucleate cell is autologous to the individual who will receive the composition. In some embodiments, the anucleate cell is allogeneic to the individual who will receive the composition.

In some embodiments, the width of the constriction is about 10% to about 99% of the mean diameter of the input anucleate cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input anucleate cells. In some embodiments, the width of the constriction about 0.25 μm to about 4 μm, about 1 μm to about 4 μm, about 1.2 μm to about 3 μm, about 1.4 μm to about 2.6 μm, about 1.6 μm to about 2.4 μm, or about 1.8 μm to about 2.2 μm. In some embodiments, the width of the constriction is about 2.0 μm. In some embodiments, the width of the constriction is about 2.5 μm. In some embodiments, the width of the constriction is about 3.0 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the cell suspension comprising the input anucleate cells are passed through multiple constrictions wherein the multiple constrictions are arranged in series and/or in parallel.

In some embodiments, the HPV antigen is a pool of multiple polypeptides that elicit a response against the same and or different HPV antigens. In some embodiments, the HPV antigen is a polypeptide comprising one or more antigenic HPV epitope and one or more heterologous peptide sequences. In some embodiments, the HPV antigen is delivered with other antigens or with an adjuvant. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV is HPV-16 or HPV-18. In some embodiments, the HPV antigen is comprised of an HLA-A2-specific epitope. In some embodiments, the HPV antigen is an HPV E6 antigen or an HPV E7 antigen. In some embodiments, the at least one antigen comprises a peptide derived from HPV E6 and/or E7. In some embodiments, the at least one antigen comprises an HLA-A2-restricted peptide derived from HPV E6 and/or E7. In some embodiments, the HPV antigen is capable of being processed into an MHC class I-restricted peptide. In some embodiments, the HPV antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

In some embodiments, there is provided a method of producing a pharmaceutical formulation of AACs, wherein the AACs comprise at least one antigen and an adjuvant, where the method comprises: a) passing a cell suspension comprising a input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed anucleate cells; and b) incubating the perturbed anucleate cells with the at least one antigen and the adjuvant for a sufficient time to allow the at least one antigen and the adjuvant to enter the perturbed anucleate cells, thereby generating the AACs comprising the at least one antigen and the adjuvant; c) washing the AACs; and d) formulating the AACs in a cryopreservation medium. In some embodiments, the AACs are washed for about any one of 1, 2, 3, 4, 5, 6, 7, 8, 9, 10, or more times. In some embodiments, the AACs are washed for about 6 times. In some embodiments, the AACs are washed in PBS. In some embodiments, the AACs are washed in medium. In some embodiments, the medium is substantially the same as medium for the input anucleate cells. In some embodiments, the AACs are washed in medium comprising one or more stabilizing agents. In some embodiments, the AACs are washed in medium comprising one or more cryopreservation agents. In some embodiments, the AACs are washed by centrifugation and resuspension. In some embodiments, the AACs are washed by centrifugation and filtration. In some embodiments, the AACs are washed by 1, 2, 3, 4, 5, 6, 7, 8, 9, 10 or more steps of centrifugation and resuspension. In some embodiments, the AACs are washed by 1, 2, 3, 4, 5, 6, 7, 8, 9, 10 or more steps of centrifugation and filtration. In some embodiments, the one or more centrifugation steps are conducted at about any one of 100×g, 150×g, 200×g, 250×g, 300×g, 350×g, 400×g, 450×g, 500×g, 550×g, 600×g, 650×g, 700×g, 750×g, and 800×g. In some embodiments, the one or more centrifugation steps are conducted at about any one of 1000 rpm, 1500 rpm, 2000 rpm, 2500 rpm, 3000 rpm, 3500 rpm, 4000 rpm, or 4500 rpm.

In some embodiments according to any one of the methods described herein, the formulation comprises about $1\times10^7$ to about $1\times10^{12}$ AACs. In some embodiments, the formulation comprises about $1\times10^9$ to about $1\times10^{11}$ AACs in about 9 mL to about 10 mL. In some embodiments, the formulation comprises about any one of $0.5\times10^7$, $0.7\times10^7$, $1.0\times10^{7}$, $0.5\times10^{8}$, $0.7\times10^{8}$, $1.0\times10^{8}$, $0.5\times10^{9}$, $0.7\times10^{9}$, $1.0\times10^{9}$, $0.5\times10^{10}$, $0.7\times10^{10}$, $1.0\times10^{10}$, $0.5\times10^{11}$, $0.7\times10^{11}$, $1.0\times10^{11}$, $0.5\times10^{12}$, $0.7\times10^{12}$, and $1.0\times10^{12}$ AACs in about 9 mL to about 10 mL. In some embodiments, the formulation comprises any one of about $0.5\times10^{7}$ to about $1.0\times10^{7}$, about $1.0\times10^{7}$ to about $0.5\times10^{8}$ AACs, about $0.5\times10^{8}$ to about $1.0\times10^{8}$, about $1.0\times10^{8}$ to about $0.5\times10^{9}$ AACs, about $0.5\times10^{9}$ to about $1.0\times10^{9}$, about $1.0\times10^{9}$ to about $0.5\times10^{10}$, about $0.5\times10^{10}$ to about $1.0\times10^{10}$, about $1.0\times10^{10}$ to about $0.5\times10^{11}$, about $0.5\times10^{11}$ to about $1.0\times10^{11}$ AACs, about $1.0\times10^{11}$ to about $0.5\times10^{12}$ AACs in about 9 mL to about 10 mL. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ AACs in about 9 mL to about 10 mL. In some embodiments, the formulation comprises about any one of $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, and $1\times10^{10}$ AACs in about 9.5 mL. In some embodiments, the formulation comprises about $7\times10^{9}$ AACs in about 9 mL to about 10 mL. In some embodiments, the formulation comprises about $7\times10^{9}$ AACs in about 9.5 mL. In some embodiments, the formulation comprises about $6.65\times10^{9}$ AACs in about 9.5 mL. In some embodiments, the formulation comprises about $0.7\times10^{9}$ AACs/mL post-thawing. In some embodiments, the formulation comprises about $0.7\times10^{9}$ AACs/mL post-thawing as measured by Coulter counter. In some embodiments, the formulation comprises about $7\times10^{9}$ AACs in about 9.5 mL of cryopreservation medium, wherein AACs comprise at least one antigen and an adjuvant, and wherein the pH of the formulation is about pH 7.6. In some embodiments, the cryopreservation medium is CryoStor® CS2.

In some embodiments, the method further comprises cryopreservation (such as freezing) of the formulation of AACs at between about −80 °C to about −250 °C. In some embodiments, the method further comprises cryopreservation (such as freezing) of the formulation of AACs at about −170 °C. In some embodiments, the method comprises freezing the formulation of AACs at about any one of −80 °C, −90 °C, −100 °C, −110 °C, −120 °C, −130 °C, −140 °C, −150 °C, −160 °C, −170 °C, −180 °C, −190 °C, −200 °C, −210 °C, −220 °C, −230°C, −240 °C or −250 °C. In some embodiments, the method comprises freezing the formulation of AACs at any one of about −80 °C to about −90 °C, about −90 °C to about −100 °C, about −100 °C to about −110 °C, about −110 °C to about −120 °C, about −120 °C to about −130 °C, about −130 °C to about −140 °C, about −140 °C to about −150 °C, about −150 °C to about −160 °C, about −160 °C to about −170 °C, about −170 °C to about −180 °C, about −180 °C to about −190 °C, about −190 °C to about −200 °C, about −200 °C to about −210 °C, about −210 °C to about −220 °C, about −220 °C to about −230 °C, about −230 °C to about −240 °C, or about −230 °C to about −240 °C.

In some embodiments, the formulation are cryopreserved (such as frozen) by a process comprising: a) placing the formulation in a chamber; b) a first step reducing the temperature of the chamber to between about 0 °C to about −20 °C; c) a second step of reducing the temperature of the chamber to between about −130 °C to about −150 °C at a rate of between about −10 °C/minute to about −30 °C/minute; d) a third step of reducing the temperature of the chamber to between about −140 °C to about −160 °C at a rate of between about −0.5 °C/minute to about −°C/minute; e) a forth step of reducing the temperature of the chamber to between about −150 °C to about −200 °C at a rate of between about −0.1 °C/minute to about −5 °C/minute; and f) holding the temperature of the chamber at between about −150 °C to about −200 °C for at least about 5 to about 30 minutes. In some embodiments, the chamber is a cryopreservation chamber, such as but not limited to a cryopreservation chamber that facilitates stable rate of temperature decrease, such as MR. FROSTY™ (Thermo Scientific™). In some embodiments, different cryopreservation chambers are used for one or more of the steps described above. In some embodiments, the formulations are subsequently removed from the chamber and moved to permanent storage (such as but not limited to liquid nitrogen tank, and such as but not limited to liquid phase, liquid-vapor transition phase or vapor phase of liquid nitrogen).

In some embodiments, the first step of reducing the temperature of the chamber of the chamber comprises reducing the temperature to any one of about 0 °C, −1 °C, −2 °C, −3 °C, or −4 °C, or any temperature or range therebetween. In some embodiments, the second step of reducing the temperature of the chamber comprises reducing the temperature of the chamber to any one of about −130 °C, −131 °C, −132 °C, −133 °C, −134 °C, −135 °C, −136 °C, −137 °C, −138°C, −139 °C, −140 °C, −141 °C, −142 °C, −143 °C, −144 °C, −145 °C, −146 °C, −147 °C, −148 °C, −149 °C, −150 °C or any temperature or range therebetween. In some embodiments, the second step of reducing the temperature of the chamber comprises reducing the temperature at a rate of any one of about −1, −2, −3, −4, −5, −6, −7, −8, −9, −10, −11, −12, −13, −14, −15, −16, −17, −18, −19, −20 °C per minute, or any rate or range therebetween. In some embodiments, the third step of reducing the temperature of the chamber comprises reducing the temperature of the chamber to any one of about −140 °C, −141 °C, −142 °C, −143 °C, −144 °C, −145 °C, −146 °C, −147 °C, −148° C, −149 °C, −150 °C, −151 °C, −152 °C, −153 °C, −154 °C, −155 °C, −156 °C, −157 °C, −158 °C, −159 °C, −160 °C or any temperature or range therebetween. In some embodiments, the third step of reducing the temperature of the chamber comprises reducing the temperature at a rate of any one of about −0.5, −1, −1.5, −2, −2.5, −3, −3.5, −4, −4.5, −5 °C per minute, or any rate or range therebetween. In some embodiments, the fourth step of reducing the temperature of the chamber comprises reducing the temperature of the chamber to any one of about −150 °C, −152 °C, −154 °C, −156 °C, −158 °C, −160 °C, −162 °C, −164 °C, −166 °C, −168 °C, −170 °C, −172 °C, −174 °C, −176 °C, −178 °C, −180 °C, −182 °C, −184 °C, −186 °C, −188 °C, −190 °C or any temperature or range therebetween. In some embodiments, the third step of reducing the temperature of the chamber comprises reducing the temperature at a rate of any one of about −0.1, −0.2, −0.3, −0.4, −0.5, −0.6, −0.7, −0.8, −0.9, −1, −1.1, −1.2, −1.3, −1.4, −1.5, −2, −2.5, −3, −3.5, −4, −4.5, −5 °C per minute. In some embodiments, the method comprises holding the temperature of the chamber at about −150 °C, −152 °C, −154 °C, −156 °C, −158 °C, −160 °C, −162 °C, −164 °C, −166 °C, −168 °C, −170 °C, −172 °C, −174 °C, −176 °C, −178 °C, −180 °C, −182 °C, −184 °C, −186 °C, −188 °C, −190 °C or any temperature or range therebetween for at least any one of about 5, 10, 15, 20, 25, 30, 35, 40, 45, 50, 55, 60 minutes or any time-intervals or range therebetween.

In some embodiments, the formulation are cryopreserved (such as frozen) by a process comprising: a) placing the formulation in a chamber; b) reducing the temperature of the chamber to about −3 °C; c) reducing the temperature of the chamber to about −140 °C at a rate of about −20 °C/minutes; d) reducing the temperature of the chamber to about −150 °C at a rate of about −1.5 °C/minutes; e) reducing the temperature of the chamber to about −170 °C at a rate of about −1.0

°C/minutes; and f) holding the temperature of the chamber at about −170 °C for at least about 10 minutes.

Antigens

In some embodiments according to the methods, formulations or vials described herein, the at least one antigen is a exogenous antigen. In some embodiments according to the methods described herein, the exogenous antigen is a HPV antigen. Papillomaviruses are small nonenveloped DNA viruses with a virion size of ~55 nm in diameter. More than 100 HPV genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN). Many of the known HPV types cause benign lesions with a subset being oncogenic. Based on epidemiologic and phylogenetic relationships, HPV types are classified into fifteen "high-risk types" (HPV 16, 18, 31, 33, 35, 39, 45, 51, 52, 56, 58, 59, 68, 73, and 82) and three "probable high-risk types" (HPV 26, 53, and 66), which together are known to manifest as low and high grade cervical changes and cancers, as well as other anogential cancers such as vulval, vaginal, penile, anal, and perianal cancer, as well as head and neck cancers. Recently, the association of high-risk types HPV 16 and 18 with breast cancer was also described. Eleven HPV types classified as "low risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness, *Am J Hematol Oncol* 13(6):20-27 (2017). In some embodiments, the exogenous antigen is a pool of multiple polypeptides that elicit a response against the same and or different antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV is HPV-16 or HPV-18. In some embodiments, the HPV antigen is comprised of an HLA-A2-specific epitope. In some embodiments, the HPV antigen is an HPV E6 antigen or an HPV E7 antigen. In some embodiments, the at least one antigen comprises a peptide derived from HPV E6 and/or E7. In some embodiments, the at least one antigen comprises an HLA-A2-restricted peptide derived from HPV E6 and/or E7. In some embodiments, the HLA-A2-restricted peptide comprises the amino acid sequence of any one of SEQ ID NOs:1-4. In some embodiments, the HLA-A2-restricted peptide comprises the amino acid sequence of any one of SEQ ID NOs:18-25. In some embodiments, the HPV antigen comprises an amino acid sequence with at least 90% similarity to any one of SEQ ID NOs:18-25. In some embodiments, the HPV antigen comprises an amino acid sequence with at least 90% similarity to SEQ ID NO:1. In some embodiments, the HPV antigen comprises an amino acid sequence with at least 90% similarity to SEQ ID NO:2. In some embodiments, the HPV antigen comprises the amino acid sequence of SEQ ID NO:3. In some embodiments, the HPV antigen comprises the amino acid sequence of SEQ ID NO:4. In some embodiment, the HPV antigen consists of the amino acid sequence of SEQ ID NO:18. In some embodiments, the HPV antigen comprises the amino acid sequence of SEQ ID NO:19. In some embodiments, the HPV antigen consists of the amino acid sequence of SEQ ID NO:20. In some embodiments, the HPV antigen consists of the amino acid sequence of SEQ ID NO:21. In some embodiments, the HPV antigen consists of the amino acid sequence of SEQ ID NO:22. In some embodiments, the HPV antigen consists of the amino acid sequence of SEQ ID NO:23. In some embodiments, the HPV antigen consists of the amino acid sequence of SEQ ID NO:24. In some embodiments, the HPV antigen consists of the amino acid sequence of SEQ ID NO:25. In some embodiments, the HPV antigen comprises the amino acid sequence of any one of SEQ ID NOs:18-25. In some embodiments, the HPV antigen is a plurality of antigens comprising at least one of the amino acid sequences of any one of SEQ ID NOs:18-25. In some embodiments, the exogenous antigen is a plurality of antigens comprising 2, 3, 4, 5, 6, 7 or 8 of the amino acid sequences of any one of SEQ ID Nos:18-25. In some embodiments, the exogenous antigen is a plurality of antigens comprising an amino acid sequence with at least 90% similarity to SEQ ID NO:19 and an amino acid sequence with at least 90% similarity to SEQ ID NO:23. In some embodiments, the exogenous antigen is a plurality of antigens comprising the amino acid sequence of SEQ ID NO:19 and the amino acid sequence of SEQ ID NO:23. In some embodiments, the plurality of antigens is contained within a pool of non-covalently linked peptides. In some embodiments, the plurality of antigens is contained within a pool of non-covalently linked peptides, wherein each peptide comprises no more than one antigen. In some embodiments, the plurality of antigens is contained within a pool of non-covalently linked peptides, wherein the amino acid sequence of SEQ ID NO:19 and the amino acid sequence of SEQ ID NO:23 are contained within separate peptides.

In some embodiments, the HPV antigen is within a pool of multiple polypeptides that elicit a response against the same and or different HPV antigens. In some embodiments, an antigen in the pool of multiple antigens does not decrease the immune response directed toward other antigens in the pool of multiple antigens. In some embodiments, the HPV antigen is a polypeptide comprising an antigenic HPV antigen and one or more heterologous peptide sequences. In some embodiments, the HPV antigen complexes with itself, with other antigens, or with the adjuvant. In some embodiments, the HPV antigen is comprised of an HLA-A2-specific epitope. In some embodiments, the HPV antigen is comprised of an HLA-A11-specific epitope. In some embodiments, HPV antigen is comprised of an HLA-B7-specific epitope. In some embodiments, the HPV antigen is comprised of an HLA-C8-specific epitope. In some embodiments, the HPV antigen comprises part or all of the N-terminal domain of a full-length HPV protein.

In some embodiments according to any one of the methods described herein, the AACs comprise a plurality of HPV antigens that comprise a plurality of immunogenic epitopes. In further embodiments, following administration to an individual of the AACs comprising the plurality of antigens that comprise the plurality of immunogenic epitopes, none of the plurality of immunogenic epitopes decreases an immune response in the individual to any of the other immunogenic epitopes. In some embodiments, the HPV antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the HPV antigen is a polypeptide comprising an immunogenic peptide epitope and one or more heterologous peptide sequences. In some embodiments, the HPV antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the HPV antigen is capable of being processed into an MHC class I-restricted peptide and/or an MHC class II-restricted peptide.

Adjuvants

As used herein, the term "adjuvant" can refer to a substance which either directly or indirectly modulates and/or engenders an immune response. In some embodiments of the invention, an adjuvant is delivered intracellularly to a population of anucleate cells or anucleate-derived vesicles such as a population of RBCs or RBC-derived vesicles (i.e, incubation of cells or vesicles with an adjuvant before, during and/or after constriction processing, but prior to administration to an individual) to form AACs comprising the adjuvant. In some instances, the adjuvant is administered in conjunction with a HPV antigen to effect enhancement of an immune response to the HPV antigen as compared to HPV antigen alone. Therefore, adjuvants can be used to boost elicitation of an immune cell response (e.g. T cell response) to a HPV antigen. Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT (SEQ ID NO:30)) or CpG ODN 2006 (also known as CpG 7909) (TCGTCGTTTTGTCGTTTTGTCGTT (SEQ ID NO:31)) oligonucleotide. In some embodiments, the adjuvant is CpG 7909. In some embodiments, the RIG-I agonist comprises polyinosinic:polycytidylic acid (polyI:C). Multiple adjuvants can also be used in conjunction with HPV antigens to enhance the elicitation of immune response. In some embodiments, the AACs comprising the HPV antigen further comprise more than one adjuvant. Multiple adjuvants can also be used in conjunction with HPV antigens to enhance the elicitation of immune response. In some embodiments, the AACs comprising the HPV antigen further comprise more than one adjuvant. In some embodiments, the AACs comprising the HPV antigen further comprise any combination of the adjuvants CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist.

Constrictions Used in Generating Compositions of AACs Comprising an Antigen and an Adjuvant In some embodiments, the invention provides formulations comprising AACs comprising at least one antigen and an adjuvant. In some embodiments, the anucleate cell is an RBC or a platelet. In some embodiments, the anucleate cell is an erythrocyte or a reticulocyte. In some embodiments, the anucleate cell is autologous to the individual who will receive the composition of AACs. In some embodiments, the anucleate cell is autologous to the individual who will receive the composition of AACs. In some embodiments, the at least one HPV antigen is delivered to the anucleate cells intracellularly. In some embodiments, the adjuvant is delivered to the anucleate cells intracellularly. Methods of introducing payloads to anucleate cells are known in the art.

In some embodiments, the HPV antigen is introduced into the anucleate cells by passing the cell through a constriction such that transient pores are introduced to the membrane of the cell thereby allowing the HPV antigen to enter the cell. Examples of constriction-based delivery of compounds into a cell are provided by WO 2013/059343, WO 2015/023982, WO 2016/070136, WO2017041050, WO2017008063, WO 2017/192785, WO 2017/192786, WO 2019/178005, WO 2019/178006, WO 2020/072833, WO 2020/154696, and WO 2020/176789, US 20180142198, and US 20180201889.

In some embodiments, the HPV antigen and adjuvant are delivered into the anucleate cells to produce the AACs of the invention by passing a cell suspension comprising the anucleate cells (e.g., RBCs) through a constriction, wherein the constriction deforms the cells thereby causing a perturbation of the cells such that a HPV antigen and an adjuvant enter the cells. In some embodiments, the constriction is contained within a microfluidic channel. In some embodiments, multiple constrictions can be placed in parallel and/or in series within the microfluidic channel.

In some embodiments, the constriction within the microfluidic channel includes an entrance portion, a center point, and an exit portion. In some embodiments, the length, depth, and width of the constriction within the microfluidic channel can vary. In some embodiments, the width of the constriction within the microfluidic channel is a function of the diameter of the anucleate cells. Methods to determine the diameter of anucleate cells are known in the art; for example, high-content imaging, cell counters or flow cytometry.

In some embodiments of the constriction-based delivery of an HPV antigen to anucleate cell-derived vesicles, the width of the constriction is about 0.5 μm to about 10 μm. In some embodiments, the width of the constriction is about 1 μm to about 4 μm. In some embodiments, the width of the constriction is about 1 μm to about 3 μm. In some embodiments, the width of the constriction is about 1.5 μm to about 2.5 μm. In some embodiments, the width of the constriction is about 1.2 μm to about 2.8 μm. In some embodiments, the width of the constriction is about 0.5 μm to about 5 μm. In some embodiments, the width of the constriction is about 2 μm to about 2.5 μm. In some embodiments, the width of the constriction is about 1.5 μm to about 2 μm. In some embodiments, the width of the constriction is about 0.5 μm to about 3.5 μm. In some embodiments, the width of the constriction is about 3.2 μm to about 3.8 μm. In some embodiments, the width of the constriction is about 3.8 μm to about 4.3 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the width of the constriction is about 2 μm. In some embodiments, the width of the constriction is about 2.2 μm. In some embodiments, the width of the constriction is about 2.5 μm. In some embodiments, the width of the constriction is about 3 μm.

Examples of parameters that may influence the delivery of the compound into the AAC include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the cell concentration, the concentration of the compound in the cell suspension, buffer in the cell suspension, and the amount of time that the AACs recover or incubate after passing through the constrictions can affect the passage of the delivered compound into the anucleate-derived vesicles. Additional parameters influencing the delivery of the compound into the AACs can include the velocity of the input anucleate cells in the constriction, the shear rate in the constriction, the viscosity of the cell suspension, the velocity component that is perpendicular to flow velocity, and time in the constriction. In addition, multiple chips comprising channels in series and/or in parallel may impact delivery to anucleate-derived vesicles. Multiple chips in parallel may be useful to enhance throughput. Such parameters can be designed to control delivery of the compound. In some embodiments, the cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 pM to at least about 2 M or any concentration or range of concentrations therebetween.

In some embodiments, the concentration of HPV antigen incubated with the anucleate cells or AACs is between about 0.01 μM and about 10 mM. For example, in some embodiments, the concentration of HPV antigen incubated with the anucleate cells or AACs is any of less than about 0.01 μM, about 0.1 μM, about 1 μM, about 10 μM, about 100 μM, about 1 mM or about 10 mM. In some embodiments, the concentration of HPV antigen incubated with the anucleate cells or AACs is greater than about 10 mM. In some embodiments, the concentration of HPV antigen incubated with the anucleate cells or AACs is any of between about 0.01 μM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of HPV antigen incubated with the anucleate cells or AACs is between about 0.1 μM and about 1 mM. In some embodiments, the concentration of HPV antigen incubated with the anucleate cells or AACs is between about 0.1 μM and about 10 μM. In some embodiments, the concentration of HPV antigen incubated with the anucleate cells or AACs is 1 μM.

In some embodiments, the concentration of antigen incubated with the perturbed input anucleate cell is between about 0.01 μM and about 10 mM. For example, in some embodiments, the concentration of antigen incubated with the perturbed input anucleate cell is any of less than about 0.01 μM, about 0.1 μM, about 1 μM, about 10 μM, about 100 μM, about 1 mM or about 10 mM. In some embodiments, the concentration of antigen incubated with the perturbed input anucleate cell is greater than about 10 mM. In some embodiments, the concentration of antigen incubated with the perturbed input anucleate cell is any of between about 0.01 μM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of antigen incubated with the perturbed input anucleate cell is between about 0.1 μM and about 1 mM. In some embodiments, the concentration of antigen incubated with the perturbed input anucleate cell is between about 0.1 μM and about 10 μM. In some embodiments, the concentration of antigen incubated with the perturbed input anucleate cell is 1 μM.

In some embodiments, the molar ratio of antigen to adjuvant incubated with the perturbed input anucleate cell is any of between about 10000:1 to about 1:10000. For example, in some embodiments, the molar ratio of antigen to adjuvant incubated with the perturbed input anucleate cell is about any of 10000:1, about 1000:1, about 100:1, about 10:1, about 1:1, about 1:10, about 1:100, about 1:1000, or about 1:10000. In some embodiments, the molar ratio of antigen to adjuvant incubated with the perturbed input anucleate cell is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the molar ratio of antigen to adjuvant incubated with the perturbed input anucleate cell is about 200:1. In some embodiments, the molar ratio of antigen to adjuvant incubated with the perturbed input anucleate cell is about 20:1.

In some embodiments, the AACs comprise the adjuvant at a concentration between about 1 nM and about 1 mM. For example, in some embodiments, the AACs comprise the adjuvant at a concentration of any of less than about 0.01 μM, about 0.1 μM, about 1 μM, about 10 μM, about 100 μM, about 1 mM or about 10 mM. In some embodiments, the AACs comprise the adjuvant at a concentration of greater than about 10 mM. In some embodiments, the AACs comprise the adjuvant at a concentration of any of between about 1 nM to about 10 nM, about 0.1 μM and about 1 μM, between about 1 μM and about 10 μM, between about 10 μM and about 100 μM, between about 100 μM and about 1 mM, or between 1 mM and about 10 mM. In some embodiments, the AACs comprise the adjuvant at a concentration between about 0.1 μM and about 1 mM. In some embodiments, the AACs comprise the adjuvant at a concentration of about 1 μM.

In some embodiments, the AACs comprise the at least one antigen at a concentration between about 1 nM and about 1 mM. For example, in some embodiments, the AACs comprises the at least one antigen at a concentration of any of less than about 0.01 μM, about 0.1 μM, about 1 μM, about 10 μM, about 100 μM, about 1 mM or about 10 mM. In some embodiments, the AACs comprise the at least one antigen at a concentration of greater than about any of 10 mM. In some embodiments, the AACs comprise the at least one antigen at a concentration of any of between about 1 nM to about 10 nM, about 0.1 μM and about 1 μM, between about 1 μM and about 10 μM, between about 10 μM and about 100 μM, between about 100 μM and about 1 mM, or between 1 mM and about 10 mM. In some embodiments, the AACs comprise the at least one antigen at a concentration between about 0.1 μM and about 1 mM. In some embodiments, the AACs comprise the at least one antigen at a concentration of about 1 μM.

In some embodiments, the molar ratio of antigen to adjuvant in the AACs is any of between about 10000:1 to about 1:10000. For example, in some embodiments, the molar ratio of antigen to adjuvant in the AACs is about any of 10000:1, about 1000:1, about 100:1, about 10:1, about 1:1, about 1:10, about 1:100, about 1:1000, or about 1:10000. In some embodiments, the molar ratio of antigen to adjuvant in the modified PBMCs is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the molar ratio of antigen to adjuvant in the AACs is about 200:1. In some embodiments, the molar ratio of antigen to adjuvant in the AACs is about 20:1.

Characteristics of AACs and Internalization by Antigen Presenting Cells

In embodiments according to any one of the methods, vials, or formulations described herein, the AACs are generated in a process comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for an antigen and an adjuvant to pass through to form perturbed input anucleate cells; b) incubating the perturbed input anucleate cells with the at least one antigen and adjuvant for a sufficient time to allow the at least one antigen and adjuvant to enter the perturbed input anucleate cells; thereby generating AACs comprising the at least one antigen and adjuvant. In some embodiments, the AACs comprising the payload (such as HPV antigen and adjuvant) displays different characteristics compared to an input anucleate cell. In some embodiments, the anucleate cell-derived vesicle comprising the payload (such as HPV antigen and adjuvant) displays different characteristics compared to an anucleate cell comprising a payload introduced by other delivery methods (such as hemolytic loading or electroporation).

In some embodiments, the half-life of the AACs following administration to a mammal is decreased compared to a half-life of the input anucleate cell following administration to the mammal. In some embodiments, the hemoglobin content of the AACs is decreased compared to the hemoglobin content of the input anucleate cell. In some embodiments, ATP production of the AACs is decreased compared to ATP production of the input anucleate cell. In some embodiments, the AACs exhibits a spherical morphology. In some embodiments, the input anucleate cell is an erythrocyte and wherein the AACs have a reduced biconcave shape compared to the input erythrocyte. In some embodiments, the AAC is a red blood cell ghost. In some embodiments, the AACs prepared by the process have greater than about 1.5 fold more phosphatidylserine on its surface compared to the input anucleate cell. In some embodiments, a population profile of AACs prepared by the process exhibits higher average phosphatidylserine levels on the surface compared to the input anucleate cells. In some embodiments, at least 50% of the population profile of AACs prepared by the process exhibits higher phosphatidylserine levels on the surface compared to the input anucleate cells. In some embodiments, the AACs exhibit preferential uptake in a tissue or cell compared to the input anucleate cell. In some embodiments, the AACs exhibit preferential uptake in phagocytic cells and/or antigen presenting cells compared to the input anucleate cell. In some embodiments, the AACs are modified to enhance uptake in a tissue or cell compared to the input anucleate cell. In some embodiments, the AACs are modified to enhance uptake in phagocytic cells and/or antigen presenting cells compared to an unmodified anucleate cell-derived vesicle. In some embodiments, the phagocytic cells and/or antigen presenting cells comprise one or more of a dendritic cell or macrophage. In some embodiments, the tissue or cell comprises one or more of liver or spleen. In some embodiments, the anucleate cell-derived vesicle comprises CD47 on its surface.

In some embodiments of the above method for generating an AAC, the constriction is contained within a microfluidic channel. In some embodiments, the microfluidic channel comprises a plurality of constrictions. In some embodiments, the plurality of constrictions is arranged in series and/or in parallel. In some embodiments, the constriction is between a plurality of micropillars; between a plurality of micropillars configured in an array; or between one or more movable plates. In some embodiments, the constriction is a pore or contained within a pore. In some embodiments, the pore is contained in a surface. In some embodiments, the surface is a filter. In some embodiments, the surface is a membrane. In some embodiments, the constriction size is a function of the diameter of the input anucleate cell in suspension. In some embodiments, the constriction size is about 10%, about 20%, about 30%, about 40%, about 50%, about 60%, or about 70% of the diameter of the input anucleate cell in suspension. In some embodiments, the constriction has a width of about 0.25 μm to about 4 μm. In some embodiments, the constriction has a width of about 4 μm, 3.5 μm, about 3 μm, about 2.5 μm, about 2 μm, about 1.5 μm, about 1 μm, about 0.5 μm, or about 0.25 μm. In some embodiments, the constriction has a width of about 2.2 μm. In some embodiments, the input anucleate cells are passed through the constriction under a pressure ranging from about 10 psi to about 90 psi. In some embodiments, said cell suspension is contacted with the at least one antigen before, concurrently, or after passing through the constriction.

In some embodiments, wherein an AAC comprising the payload (e.g. at least one HPV antigen and an adjuvant) is prepared from an input anucleate cell, the AAC having one or more of the following properties: (a) a circulating half-life in a mammal is decreased compared to the input anucleate cell, (b) decreased hemoglobin levels compared to the input anucleate cell, (c) spherical morphology, (d) increased surface phosphatidylserine levels compared to the input anucleate cell, or (e) reduced ATP production compared to the input anucleate cell.

In some embodiments, the input anucleate cell is a mammalian cell. In some embodiments, the input anucleate cell is human cell. In some embodiments, the input anucleate cell is a red blood cell or a platelet. In some embodiments, the red blood cell is an erythrocyte or a reticulocyte. In some embodiments, the anucleate cell is autologous to the individual who will receive the composition. In some embodiments, the anucleate cell is autologous to the individual who will receive the composition.

In some embodiments, the circulating half-life of the AAC in a mammal is decreased compared to the input anucleate cell. In some embodiments, the circulating half-life in the mammal is decreased by more than about 50%, about 60%, about 70%, about 80%, about 90%, about 95%, about 96%, about 97%, about 98%, or about 99% compared to the input anucleate cell.

In some embodiments, the input anucleate cell is a human cell and wherein the circulating half-life of the AAC is less than about 1 minute, about 2 minutes, about 5 minutes, about 10 minutes, about 15 minutes, about 30 minutes, about 1 hour, about 6 hours, about 12 hours, about 1 day, about 2 days, about 3 days, about 4 days, about 5 days, about 10 days, about 25 days, about 50 days, about 75 days, about 100 days, about 120 days.

In some embodiments, the input anucleate cell is a red blood cell, wherein the hemoglobin levels in the AAC are decreased compared to the input anucleate cell. In some embodiments, the hemoglobin levels in the AAC are decreased by at least about 10%, about 20%, about 30%, about 40%, about 50%, about 60%, about 70%, about 80%, about 90%, about 99% or about 100% compared to the input anucleate cell. In some embodiments, the hemoglobin levels in the AAC are about 1%, about 5%, about 10%, about 20%, about 30%, about 40%, or about 50% the level of hemoglobin in the input anucleate cell.

In some embodiments, the input anucleate cell is an erythrocyte and wherein the AAC is spherical in morphology. In some embodiments, the input anucleate cell is an erythrocyte and wherein the AAC has a reduced biconcave shape compared to the input anucleate cell.

In some embodiments, the input anucleate cell is a red blood cell or an erythrocyte and wherein the AAC is a red blood cell ghost (RBC ghost).

In some embodiments, the AAC comprises CD47 on its surface.

In some embodiments, the AAC has increased surface phosphatidylserine levels compared to the input anucleate cell. In some embodiments, the AACs prepared by the process has greater than about 1.5 fold more phosphatidylserine on its surface compared to the input anucleate cell. In some embodiments, the AAC has about 10%, about 20%, about 30%, about 40%, about 50%, about 60%, about 70%, about 80%, about 90%, about 99%, about 100% or more than about 100% more phosphatidylserine on its surface compared to the input anucleate cell.

In some embodiments, the AAC has reduced ATP production compared to the input anucleate cell. In some embodiments, the AAC produces ATP at less than about 1%, about 5%, about 10%, about 20%, about 30%, about 40%, or about 50% the level of ATP produced by the input anucleate cell. In some embodiments, the AAC does not produce ATP.

In some embodiments, the AAC exhibits enhanced uptake in a tissue or cell compared to the input anucleate cell. In some embodiments, the AAC exhibits preferential uptake in liver or spleen or by a phagocytic cell or an antigen-presenting cell compared to the uptake of the input anucleate cell.

In some embodiments, the AAC is further modified to enhance uptake in a tissue or cell compared to the input anucleate cell. In some embodiments, the AAC is further modified to enhance uptake in liver or spleen or by a phagocytic cell or an antigen-presenting cell compared to the uptake of the input anucleate cell.

In some embodiments, wherein the AAC exhibits enhanced uptake in liver or spleen or by a phagocytic cell and/or an antigen-presenting cell, internalization of the AAC results in increased expression of maturation markers of the phagocytic cell or the antigen-presenting cell. In some embodiments, the phagocytic cell and/or the antigen-presenting cell is a monocyte-derived dendritic cell (MODC). In some embodiments, the maturation marker is one or more of CD80, CD86, CD83, and MHC-II. In some embodiments, the expression of one or more of CD80, CD86, CD83, and MHC-II is increased in the phagocytic cell and/or the antigen-presenting cell contacted with an AAC comprising a HPV antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or an antigen-presenting cell not contacted with a AAC comprising a HPV antigen. In some embodiments, the expression of one or more of CD80, CD86, CD83, and MHC-II is increased in the phagocytic cell and/or the antigen-presenting cell contacted with an AAC comprising a HPV antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or an antigen-presenting cell contacted with the input anucleate cell.

In some embodiments, wherein the AAC comprising an HPV antigen, or a HPV antigen and adjuvant exhibits enhanced uptake in liver or spleen or by a phagocytic cell and/or an antigen-presenting cell, internalization of the AAC results in increased presentation of the HPV antigen comprised within the anucleate cell-derived vesicle. In some embodiments, the presentation of the HPV antigen is increased in the phagocytic cell and/or the antigen-presenting cell contacted with a AAC comprising a HPV antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or an antigen-presenting cell contacted with corresponding anucleate cells comprising the same HPV antigen introduced by other delivery methods (such as but not limited to hemolytic loading).

In some embodiments, wherein the AAC comprising an HPV antigen, or a HPV antigen and adjuvant exhibits enhanced uptake in liver or spleen or by a phagocytic cell and/or an antigen-presenting cell, internalization of the AAC results in increased ability of the phagocytic cell and/or the antigen-presenting cell to induce an antigen-specific immune response. In some embodiments, the antigen-specific immune response mediated by the phagocytic cell and/or the antigen-presenting cell contacted with a AAC comprising the HPV antigen or the HPV antigen and adjuvant is increased by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or an antigen-presenting cell contacted with the input anucleate cells. In some embodiments, the antigen-specific immune response mediated by the phagocytic cell and/or the antigen-presenting cell contacted with a AAC comprising the HPV antigen or the HPV antigen and adjuvant is increased by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or an antigen-presenting cell contacted with the anucleate cells comprising the same HPV antigen introduced by other delivery methods (such as but not limited to hemolytic loading). In some embodiments, the antigen-specific immune response is an antigen-specific CD4+ T cell response. In some embodiments, the antigen-specific immune response is an antigen-specific CD8+ T cell response.

In some embodiments, the individual is positive for HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, and/or HLA-C*16.

In some embodiments according to any one of the methods, compositions, or uses described herein, the phagocytes are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, and/or HLA-C*16. In some embodiments, the antigen presenting cells are human cells with a haplotype of HLA-A*02, HLA-A*11, HLA-B*07, or HLA-C*08. In some embodiments, HPV antigens presented by the phagocytes and/or antigen presenting cells described herein are comprised of an HLA-A2-specific epitope. In some embodiments, HPV antigens presented by the phagocytes and/or antigen presenting cells described herein are comprised of an HLA-A11-specific epitope. In some embodiments, HPV antigens presented by the phagocytes and/or antigen presenting cells described herein are comprised of an HLA-B7-specific epitope. In some embodiments, HPV antigens presented by the phagocytes and/or antigen presenting cells described herein are comprised of an HLA-C8-specific epitope.

In some embodiments, the method comprises administering AACs comprising the HPV antigen and adjuvant to the individual, wherein the AACs are internalized by phagocytic cells and/or antigen-presenting cell. In some embodiments, wherein the AACs are internalized by phagocytic cells and/or antigen-presenting cell, internalization of the AAC results in increased expression of maturation markers of the phagocytic cell or the antigen-presenting cell. In some embodiments, the phagocytic cell and/or the antigen-presenting cell is a monocyte-derived dendritic cell (MODC). In some embodiments, the maturation marker is one or more of CD80, CD86, CD83, and MHC-II. In some embodiments, the expression of one or more of CD80, CD86, CD83, and MHC-II is increased in the phagocytic cell and/or the antigen-presenting cell contacted with a AAC comprising a HPV antigen by at least about any one of: 10%, 20%, 50%, 80%, 100%, 2-fold, 5-fold, 10-fold, 20-fold, 50-fold, 100-fold, 1000-fold, 10000-fold or more compared to an phagocytic cell and/or an antigen-presenting cell not contacted with a AAC comprising a HPV antigen. In some embodiments, the expression of one or more of CD80, CD86, CD83, and MHC-II is increased in the phagocytic cell and/or the antigen-presenting cell contacted with a AAC comprising a HPV antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or an antigen-presenting cell contacted with the input anucleate cell.

In some embodiments, the input anucleate cell was not (a) heat processed, (b) chemically treated, and/or (c) subjected to hypotonic or hypertonic conditions during the preparation of the anucleate cell-derived vesicles. In some embodiments, osmolarity was maintained during preparation of the AAC from the input anucleate cell. In some embodiments, the osmolarity was maintained between about 200 mOsm and about 600 mOsm. In some embodiments, the osmolarity was maintained between about 200 mOsm and about 400 mOsm.

Systems and Kits

In some aspects, the invention provides a system comprising one or more of the constriction, an anucleate cell suspension, antigens or adjuvants for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to anucleate cells. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in treating individuals with a cancer associated with HPV. In some embodiments, the kit comprises an AAC comprising intracellularly an antigen and intracellularly an adjuvant. In some embodiments, the kit comprises one or more of the constriction, an anucleate cell suspension, HPV antigens or adjuvants for use in generating AACs for use in treating an individual with a disease associated with HPV, such as cancer. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods treat an individual with a cancer associated with HPV and/or instructions for introducing a HPV antigen and an adjuvant into an anucleate cell. The kits described herein may further include other materials, including other buffers, diluents, filters, needles, syringes, and package inserts with instructions for performing any methods described herein; e.g., instructions for treating an individual with a cancer associated with HPV or instructions for generating AACs to contain intracellularly a HPV antigen and intracellularly an adjuvant.

Exemplary Embodiments

Embodiment 1. A pharmaceutical formulation comprising activating antigen carriers (AACs), the formulation comprising a) AACs wherein the AACs comprise at least one antigen and an adjuvant, and b) a cryopreservation medium.

Embodiment 2. The pharmaceutical formulation of embodiment 1, wherein the formulation comprises about $0.5\times10^9$ AACs to about $1\times10^{10}$ AACs.

Embodiment 3. The pharmaceutical formulation of embodiment 1 or 2, wherein the formulation comprises about $7\times10^9$ AACs.

Embodiment 4. The pharmaceutical formulation of any one of embodiments 1-3, wherein the formulation comprises about $7\times10^9$ AACs prior to freezing.

Embodiment 5. The pharmaceutical formulation of any one of embodiments 1-4, wherein the formulation comprises AACs that were previously frozen, wherein the formulation comprises about $9\times10^9$ AACs after thawing.

Embodiment 6. The pharmaceutical formulation of any one of embodiments 1-5, wherein the formulation comprises about $0.5\times10^9$ AACs/mL to about $1\times10^9$ AACs/mL.

Embodiment 7. The pharmaceutical formulation of any one of embodiments 1-6, wherein the formulation comprises about $0.7\times10^9$ AACs/mL.

Embodiment 8. The pharmaceutical formulation of any one of embodiments 1-7, wherein the formulation comprises about $0.7\times10^9$ AACs/mL prior to freezing.

Embodiment 9. The pharmaceutical formulation of any one of embodiments 1-8, wherein the formulation comprises AACs that were previously frozen, wherein the formulation comprises about $1\times10^9$ AACs/mL after thawing.

Embodiment 10. The pharmaceutical formulation of any one of embodiments 1-9, wherein at least about 70%, 80%, 90%, or 95% of AACs of a population of the AACs are functional.

Embodiment 11. The pharmaceutical formulation of any one of embodiments 1-10, wherein the AACs in the formulation maintain equal to or greater than about 70% functionality.

Embodiment 12. The pharmaceutical formulation of any one of embodiments 1 or 2, wherein the formulation comprises about $1\times10^8$ functional AACs/mL to about $1\times10^9$ functional AACs/mL.

Embodiment 13. The pharmaceutical formulation of any one of embodiments 1-12, wherein at least about 70%, 80%, 90%, or 95% of AACs of a population of the AACs are positive for annexin staining.

Embodiment 14. The pharmaceutical formulation of any one of embodiments 1-13, wherein the AACs in the formulation maintain equal to or greater than about 70% are positive for annexin staining.

Embodiment 15. The pharmaceutical formulation of embodiment 13 or 14, wherein the annexin is annexin V.

Embodiment 16. The pharmaceutical formulation of any one of embodiments 1-15, wherein the cryopreservation medium comprises dimethylsulfoxide (DMSO).

Embodiment 17. The pharmaceutical formulation of any one of embodiments 1-16, wherein the cryopreservation medium comprises about 0.5% to about 5% DMSO.

Embodiment 18. The pharmaceutical formulation of any one of embodiments 1-17, wherein the cryopreservation medium comprises about 2% DMSO.

Embodiment 19. The pharmaceutical formulation of any one of embodiments 1-18, wherein the cryopreservation medium is CryoStor® CS2.

Embodiment 20. The pharmaceutical formulation of any one of embodiments 1-19, wherein the pH of the formulation is about 6.0 to about 8.5.

Embodiment 21. The pharmaceutical formulation of any one of embodiments 1-20, wherein the pH of the formulation is about 7.6.

Embodiment 22. A pharmaceutical formulation of AACs, the formulation comprising about $0.5\times10^9$ AACs to about $1\times10^{10}$ AACs in cryopreservation medium, wherein AACs comprise at least one antigen and an adjuvant, wherein the pH of the formulation is about pH 6.0 to about pH 8.5.

Embodiment 23. A pharmaceutical formulation of AACs, the formulation comprising about $0.5\times10^9$ AACs to about $1\times10^{10}$ AACs in a cryopreservation medium, wherein AACs comprise at least one antigen and an adjuvant, wherein the pH of the formulation is about pH 7.6.

Embodiment 24. The pharmaceutical formulation of embodiment 22 or 23 wherein the formulation comprises about $7\times10^9$ AACs prior to freezing.

Embodiment 25. The pharmaceutical formulation of any one of embodiments 22-25, wherein the formulation comprises AACs that were previously frozen, wherein the formulation comprises about $9\times10^9$ cells after thawing.

Embodiment 26. The pharmaceutical formulation of any one of embodiments 22-25, wherein the formulation comprises about $0.5\times10^9$ AACs/mL to about $1\times10^9$ AACs/mL.

Embodiment 27. The pharmaceutical formulation of any one of embodiments 22-26, wherein the formulation comprises about $0.7\times10^9$ AACs/mL.

Embodiment 28. The pharmaceutical formulation of any one of embodiments 22-27, wherein the formulation comprises about $0.7\times10^9$ AACs/mL prior to freezing.

Embodiment 29. The pharmaceutical formulation of any one of embodiments 22-28, wherein the formulation comprises AACs that were previously frozen, wherein the formulation comprises about $1\times10^9$ AACs/mL after thawing.

Embodiment 30. A pharmaceutical formulation of AACs, the formulation comprising about $7\times10^9$ AACs in about 9.5 mL of cryopreservation medium, wherein AACs comprise at least one antigen and an adjuvant, and wherein the pH of the formulation is about pH 7.6.

Embodiment 31. The pharmaceutical formulation of any one of embodiments 22-30, wherein the cryopreservation medium is CryoStor® CS2.

Embodiment 32. The pharmaceutical formulation of any one of embodiments 1-31, wherein the formulation is sterile.

Embodiment 33. The pharmaceutical formulation of any one of embodiments 1-32, wherein the formulation comprises less than about 2 EU/mL endotoxin.

Embodiment 34. The formulation of any one of embodiments 1-33, wherein the formulation is free of mycoplasma.

Embodiment 35. The formulation of any one of embodiments 1-34, wherein the at least one antigen is a human papillomavirus (HPV) antigen.

Embodiment 36. The formulation of embodiment 35, wherein the HPV is HPV-16 or HPV-18.

Embodiment 37. The formulation of embodiment 35 or 36, wherein the antigen comprises a peptide derived from HPV E6 and/or E7.

Embodiment 38. The formulation of any one of embodiments 35-37, wherein the antigen comprises a peptide derived from HPV E6 and a peptide from HPV E7.

Embodiment 39. The formulation of any one of embodiments 35-38, wherein the antigen comprises the amino acid sequence of any one of SEQ ID NOs: 1-4.

Embodiment 40. The formulation of any one of embodiments 35-39, wherein the antigen comprises the amino acid sequence of any one of SEQ ID NOs:18-25.

Embodiment 41. The formulation of any one of embodiments 35-40, wherein the AACs comprises an antigen comprising the amino acid sequence of SEQ ID NO:19 and an antigen comprising the amino acid sequence of SEQ ID NO:23.

Embodiment 42. The formulation of any one of embodiments 1-41, wherein the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist.

Embodiment 43. The formulation of embodiment 42, wherein the adjuvant is a CpG 7909 oligodeoxynucleotide (ODN).

Embodiment 44. The formulation of any one of embodiments 1-43, wherein the AACs comprising the at least one antigen and an adjuvant are prepared by a process comprising:

a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed anucleate cells; and b) incubating the perturbed anucleate cells with the at least one antigen and the adjuvant for a sufficient time to allow the at least one antigen and the adjuvant to enter the perturbed anucleate cells, thereby generating the AACs comprising the at least one antigen and the adjuvant.

Embodiment 45. The method of embodiment 44, wherein the diameter of the constriction is about 1.6 μm to about 2.4 μm or about 1.8 μm to about 2.2 μm.

Embodiment 46. The method of embodiment 44 or 45, wherein the input anucleate cell is a red blood cell.

Embodiment 47. A vial comprising the pharmaceutical formulation of any one of embodiments 1-46.

Embodiment 48. A vial comprising a pharmaceutical formulation; the pharmaceutical formulation comprising about $1\times10^9$ AACs to about $1\times10^{10}$ AACs in cryopreservation medium, wherein AACs comprise at least one antigen and an adjuvant, wherein the pH of the formulation is about pH 6.0 to about pH 8.5.

Embodiment 49. A vial comprising a pharmaceutical formulation; the pharmaceutical formulation comprising about $1\times10^9$ AACs to about $1\times10^{10}$ AACs in a cryopreservation medium, wherein AACs comprise at least one antigen and an adjuvant, wherein the pH of the formulation is about pH 7.6.

Embodiment 50. The vial of embodiment 48 or 49 wherein the formulation comprises about $7\times10^9$ AACs prior to freezing.

Embodiment 51. The vial of any one of embodiments 48-50, wherein the formulation comprises AACs that were previously frozen, wherein the formulation comprises about $9\times10^9$ cells after thawing.

Embodiment 52. The vial of any one of embodiments 48-51, wherein the formulation comprises about $0.5\times10^9$ AACs/mL to about $1\times10^9$ AACs/mL.

Embodiment 53. The vial of any one of embodiments 48-52, wherein the formulation comprises about $0.7\times10^9$ AACs/mL.

Embodiment 54. The vial of any one of embodiments 48-53, wherein the formulation comprises about $0.7\times10^9$ AACs/mL prior to freezing.

Embodiment 55. The vial of any one of embodiments 48-54, wherein the formulation comprises AACs that were previously frozen, wherein the formulation comprises about $1\times10^9$ AACs/mL after thawing.

Embodiment 56. A vial comprising a pharmaceutical formulation; the pharmaceutical formulation comprising about $7\times10^9$ AACs in about 9.5 mL of cryopreservation medium, wherein AACs comprise at least one antigen and an adjuvant, and wherein the pH of the formulation is about pH 7.6.

Embodiment 57. The vial of any one of embodiments 48-56 or 39, wherein the AACs are in about 9.5 mL of the cryopreservation medium.

Embodiment 58. A vial comprising a pharmaceutical formulation; the pharmaceutical formulation comprising about $7\times10^9$ AACs in about 9.5 mL of cryopreservation medium, wherein AACs comprise at least one antigen and an adjuvant, and wherein the pH of the formulation is about pH 7.6.

Embodiment 59. The vial of any one of embodiments 47-58, wherein the formulation is sterile.

Embodiment 60. A method of producing a pharmaceutical formulation of AACs, the method comprising adding a cryopreservation medium to the AACs wherein the AACs comprise at least one antigen and an adjuvant.

Embodiment 61. A method of producing a pharmaceutical formulation of AACs, wherein the AACs comprise the at least one antigen and an adjuvant, the method comprising:

a) passing a cell suspension comprising a input anucleate cells through a cell-deforming constriction, wherein a diameter of the constriction is a function of a diameter of the input anucleate cells in the suspension, thereby causing perturbations of the input anucleate cells large enough for the at least one antigen and the adjuvant to pass through to form perturbed anucleate cells; and b) incubating the perturbed anucleate cells with the at least one antigen and the adjuvant for a sufficient time to allow the at least one antigen and the adjuvant to enter the perturbed anucleate cells, thereby generating the AACs comprising the at least one antigen and the adjuvant;

c) washing the AACs; and d) formulating the AACs in a cryopreservation medium.

Embodiment 62. The method of embodiment 61, wherein the diameter of the constriction is about 1.6 μm to about 2.4 μm or about 1.8 μm to about 2.2 μm.

Embodiment 63. The method of embodiment 61 or 62, wherein the AACs are washed about 6 times.

Embodiment 64. The method of any one of embodiments 61-63, wherein the AACs are washed by centrifugation and resuspension or by centrifugation and filtration.

Embodiment 65. The method of embodiment 64, wherein the centrifugation is at about 4000 rpm.

Embodiment 66. The method of any one of embodiments 61-65, wherein about $1\times10^9$ AACs to about $1\times10^{10}$ AACs are formulated in about 9 mL to about 10 mL of the cryopreservation medium.

Embodiment 67. The method of embodiment 66, wherein the pharmaceutical formulation comprises about $7\times10^9$ AACs prior to freezing.

Embodiment 68. The method of embodiment 66 or 67, wherein the formulation comprises AACs that were previously frozen, wherein the formulation comprises about $9\times10^9$ cells after thawing.

Embodiment 69. The method of any one of embodiments 66-68, wherein the formulation comprises about $0.5\times10^9$ AACs/mL to about $1\times10^9$ AACs/mL.

Embodiment 70. The method of any one of embodiments 66-69, wherein the formulation comprises about $0.7\times10^9$ AACs/mL.

Embodiment 71. The method of any one of embodiments 66-70, wherein the formulation comprises about $0.7\times10^9$ AACs/mL prior to freezing.

Embodiment 72. The method of any one of embodiments 66-71, wherein the formulation comprises AACs that were previously frozen, wherein the formulation comprises about $1\times10^9$ AACs/mL after thawing.

Embodiment 73 The method of any one of embodiments 66-72, wherein about $7\times10^9$ AACs are formulated in about 10 mL of the cryopreservation medium.

Embodiment 74. The method of any one of embodiments 66-73, wherein the cryopreservation medium is CryoStor® CS2.

Embodiment 75. The method of any one of embodiments 61-74, wherein the input anucleate cell is a red blood cell.

Embodiment 75. The method of any one or embodiments 60-75, wherein the method further comprises freezing the formulation of AACs at about −170 °C.

Embodiment 76. The method of embodiment 75, where the formulation of AACs are frozen by a process comprising:

a) placing the formulation in a chamber b) reducing the temperature of the chamber to about −3 °C c) reducing the temperature of the chamber to about −140 °C at a rate of about −20 °C/minutes d) reducing the temperature of the chamber to about −150 °C at a rate of about 1.5 °C/minutes.

e) reducing the temperature of the chamber to about −170 °C at a rate of about 1.0 °C/minutes, and f) holding the temperature of the chamber at about −170 °C for at least about 10 minutes.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1. Development of AAC-HPV

For the development of an AAC-HPV drug substance manufacturing process, process development studies were executed using whole blood collected from healthy donors and shipped overnight at refrigerated conditions (2-8 °C) to the manufacturer.

Whole Blood Dilution

Upon receipt of the blood bag inside the manufacturing suite, the starting material information was verified against the manufacturing batch record. A sample was aseptically withdrawn from the blood bag and a complete blood count (CBC) measurement is obtained via a hematology analyzer for information only, as well as an RBC count using a Coulter-based cell counter where the tentative criterion for total number of RBCs is $\geq5\times10^{11}$ total RBCs.

Following sample collection, the starting whole blood was diluted with RPMI+5% DMSO (dilution media) to reduce the cell concentration for processing on a LOVO cell washing system. The dilution media contains 5% DMSO to be similar to the media required for dissolution of the SLPs & adjuvant used in the delivery process downstream of this unit operation.

Whole Blood Dilution Ratio Prior to LOVO Cell Washing

An assessment of the whole blood dilution ratio was performed. For the purposes of this evaluation, whole blood collected from several healthy donors was diluted with dilution media at different ratios and processed on the LOVO. LOVO parameters recommended by the equipment vendor (Fresenius Kabi) for platelet removal were used for this evaluation. Following cell washing, the collected product was assessed for cell count and stepwise recovery for RBCs was calculated. RBC recovery results from different whole blood dilution ratio evaluations are shown in Table 1. The measurement shown were obtained from either a Coulter-based cell counter or a complete blood count using a hematology analyzer.

TABLE 1

Whole Blood Dilution Ratio Evaluation Results

| Experiment # | Starting Cell Count (RBCs) | Starting Whole Blood Volume (mL) | Dilution Media Volume (mL) | Dilution Ratio | LOVO Output Cell Count (RBCs) | RBC Recovery |
|---|---|---|---|---|---|---|
| 1072 | $7.90\times10^{11}$ | 200 | 800 | 1:4 | $7.09\times10^{11}$ | 90% |
| | $3.90\times10^{11}$ | 100 | 900 | 1:9 | $3.63\times10^{11}$ | 93% |
| 1809 | $1.20\times10^{12}$ | 323 | 1000 | 1:3.1 | $1.16\times10^{12}$ | 96% |
| 2249 | $7.95\times10^{11}$ | 152 | 456 | 1:3 | $7.81\times10^{11}$ | 98% |
| | $7.93\times10^{11}$ | 168 | 504 | 1:3 | $7.32\times10^{11}$ | 92% |

As shown in Table 1, dilution ratios from 1:3 to 1:9 all show similar RBC recoveries over the LOVO process. For the SQZ-AAC-HPV process, the expected patient starting material (whole blood including anticoagulant) volume is 260 to 270 mL, and a set dilution media volume of 1 L was implemented to simplify the manufacturing process. The final parameters for the whole blood dilution step are shown in Table 2. Following whole blood dilution, the intermediate product is gravity filtered through a sterile single-use 40 μm blood filter to remove any potential cell aggregates.

TABLE 2

Whole Blood Dilution Parameters

| Dilution media | Dilution volume (mL) | Expected whole blood volume (mL) |
|---|---|---|
| RPMI + 5% DMSO | 1000 | Approximately 200[a] |

[a]Patient starting material will include approximately an additional 60-70 mL of anticoagulant for a total expected volume of 260-270 mL RBC Purification & Peptide+Adjuvant Introduction A sample was aseptically withdrawn from the diluted blood bag and an RBC count is taken. The diluted blood is then processed on the LOVO cell washing system where the cells are washed for platelet removal with a sterile filtered mixture of 50 μM E6 SLP, 250 μM E7 SLP and 1.5 mg/mL poly I:C in RPMI 1640 Medium with 5% DMSO (referred to as the delivery media). After platelet removal, the cells were resuspended with the delivery media using the LOVO system. Following resuspension with delivery media, the in-process material was aseptically processed through a leukoreduction filter where WBCs are removed, resulting in a purified RBC suspension in delivery media. The purified cell suspension was then assessed for RBC count and complete blood count (FIO) that captures WBCs and platelets. All processing occurred at ambient conditions.

RBC Purification—Platelet Removal & Peptide+Adjuvant Introduction

Following whole blood dilution, RBCs were washed and resuspended with delivery media using the LOVO system at ambient conditions. The LOVO system utilizes a single-use LOVO kit which consists of a 4 μm spinning membrane, allowing for removal of platelets while maximizing recovery of RBCs. Using variable inlet and outlet flow rates, the LOVO system allows for washing and concentration of cells. Processing parameters used on the LOVO system for washing and resuspending RBCs with delivery media were provided by the equipment vendor (Fresenius Kabi). The recommended parameters provided by the vendor were evaluated during the development activities.

An assessment of platelet removal and RBC recovery was performed over the LOVO process taken from 7 different healthy donors. The unit operation demonstrated a mean RBC recovery of 89.12±5.75% and mean platelet removal of 74.56±10.52% as shown in FIG. 1. The LOVO processing parameters for platelet removal are provided in Table 3.

TABLE 3

LOVO Processing Parameters for Washing and SLP & Adjuvant Introduction

| Cycle | Spinner Rate (rpm) | Inlet Flow Rate (mL/min) | Outlet Flow Rate (mL/min) | Final Output Volume (mL) |
|---|---|---|---|---|
| Cycle 1 | 4000 | 60 | 10 | N/A |
| Cycle 2 | 4000 | 30 | 10 | 230 |

RBC Purification—Leukoreduction (WBC Removal)

Following the wash and resuspension of RBCs into delivery media, the intermediate product is filtered through a sterile single-use leukoreduction-filtration assembly at ambient conditions. The filtration assembly consists of a leukoreduction filter (LRF), a 40 μm blood filter and an 18 μm blood filter assembled in line. The leukoreduction-filtration assembly allows for removal of WBCs, and any potential cell aggregates. It has been noted that the leukoreduction filter also removes platelets in a non-specific manner. Initial trial runs with the leukoreduction filtration step attempted to leukoreduce the incoming donor whole blood prior to other handling, however the filtration time was observed to be prohibitively long in duration. Ultimately it was determined that the leukoreduction step was best suited after the initial RBC purification on the LOVO had occurred, reducing the filtration time to <5 minutes.

Figure 2:
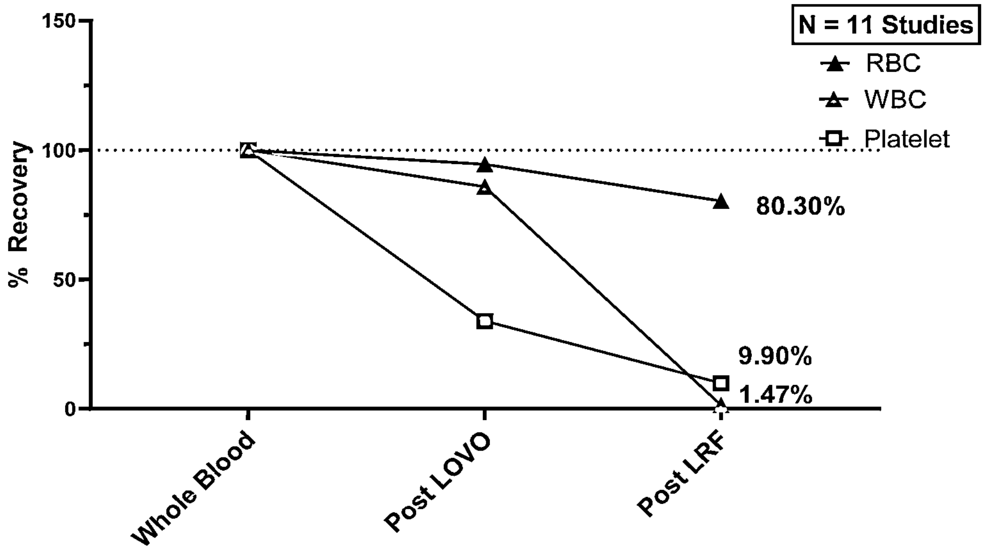
FIG. 2 shows average overall recovery of RBCs, platelets, and white blood cells of eleven runs over the RBC purification step encompassing cell washing and resuspension with delivery media on the LOVO and purification via the leukoreduction filter.

FIG. 2 shows the average overall recovery of RBCs, platelets, and WBCs of n=11 runs over the RBC purification step encompassing cell washing and resuspension with delivery media on the LOVO and purification via the leukoreduction filter. The data demonstrates suitable RBC purification in preparation for peptide & adjuvant delivery in the subsequent processing steps. Peptide (E6 and E7 SLPs) & Adjuvant (Poly I:C) Delivery A microfluidic chip with a 2.2 μm constriction was used for the development of the RBC delivery process. The microfluidic chip was selected to align with the chip constriction width used during the pre-clinical research studies. It is noted that the small number of residual WBCs remaining (see FIG. 2) in-process during manufacture of AAC-HPV prior to the delivery step do not clog the chip.

Preliminary studies to identify the suitable delivery parameters were conducted with fluorescently labeled Ovalbumin (Ovalbumin 647) as surrogate delivery material. Once the initial design space was established, confirmatory studies were conducted with fluorescently labeled E6 & E7 SLPs (FAM-E6 and FAM-E7). Poly I:C was also used as a delivery material but was not measured in these studies as fluorescently labeled poly I:C was not available.

```
                                        (SEQ ID NO: 19)
    E6 SLP: QLCTELQTTIHDIILECVYCKQQLL

                                        (SEQ ID NO: 23)
    E7 SLP: QLCTELQTYMLDLQPETTYCKQQLL
```

Preliminary Delivery Evaluations with Ovalbumin 647

A target operating temperature of 2-8 °C based on pre-clinical research-scale delivery studies. RBC delivery using Ovalbumin 647 was analyzed using flow cytometry to measure cell delivery of Ovalbumin 647 and Annexin V+ phenotype (a measure of phosphatidylserine on the membrane outer leaflet) for each study.

Pressure Evaluation & Microfluidic Chip Configuration

A study of operating pressure & microfluidic chip configuration was performed to evaluate Ovalbumin 647 delivery and Annexin V positivity at different operating pressures and utilizing a different number of 2.2 μm constriction chips arranged in parallel. The study evaluated three discrete chip configurations of the same chip type (1 chip, 2× chips in parallel, 4× chips in parallel) and two operating pressures (60 psi, 75 psi).

Figure 3A:
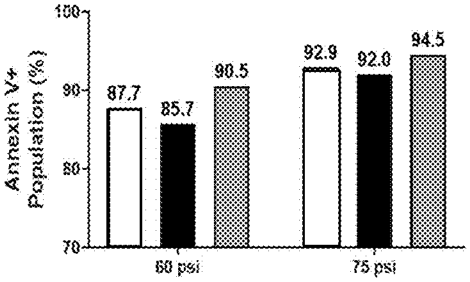
FIG. 3A shows an increase in Annexin V+ population following passage of red blood cells through different chip configurations at 60 psi and 75 psi operating pressure.
Figure 3B:
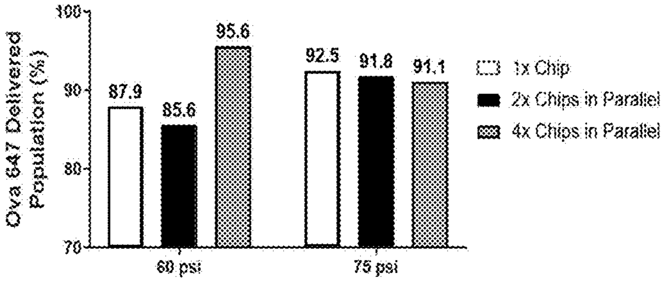
FIG. 3B shows delivery of Ova647 following passage of red blood cells through different chip configurations at 60 psi and 75 psi operating pressure.

FIG. 3 shows an increase in Annexin V+ population in the study arm performed at 75 psi operating pressure compared to the study arm performed at 60 psi operating pressure. Additionally, the population delivered with Ovalbumin 647 at the 75 psi operating pressure showed most consistent results (>90% delivery) across all three chip configurations tested. As a result of this evaluation, the operating pressure of 75 psi and the 4× chip configuration was selected to maximize intracellular delivery and throughput of the delivery process.

Cell Concentration Evaluation

Due to the variable incoming red blood cell count from each donor, a range of cell concentrations is expected for the Peptide & Adjuvant Delivery process. An evaluation was performed of various cell concentrations. Red blood cells at various concentrations were processed with Ovalbumin 647 as the delivery material through 4× chips in parallel at 75 psi operating pressure and analyzed for delivery.

Figure 4:
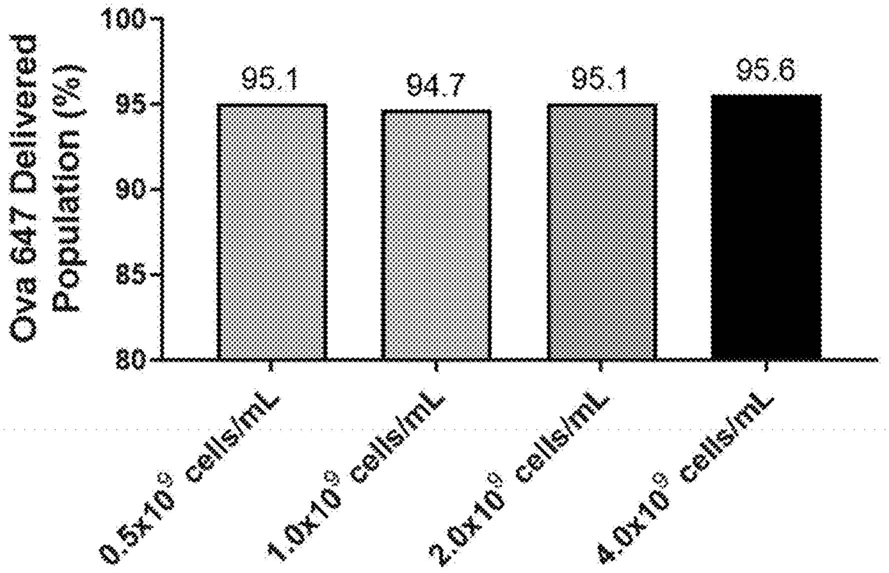
FIG. 4 shows delivery of Ova647 following passage of red blood cells through a chip a different cell concentrations.

FIG. 4 results show that delivery using the previously selected operating parameters is consistent across cell concentrations ranging from $0.5\times10^9$ to $4.0\times10^9$ RBCs/mL. As a result of this evaluation, the operating range for RBC delivery with SLPs & adjuvant was established for the cell concentrations tested. The cell concentration in the SQZ-AAC-HPV manufacturing process is expected to fall within the range tested.

Delivery Evaluations with Labeled Peptides (FAM-E6 and FAM-E7 SLPs) & Poly I:C Content Following the preliminary studies using Ovalbumin 647, confirmatory studies were performed using FAM labeled E6 & E7 SLPs and non-labeled poly I:C. Studies were performed using the delivery parameters (4× chip configuration, 75 psi, 2-8 °C).

Figure 5:
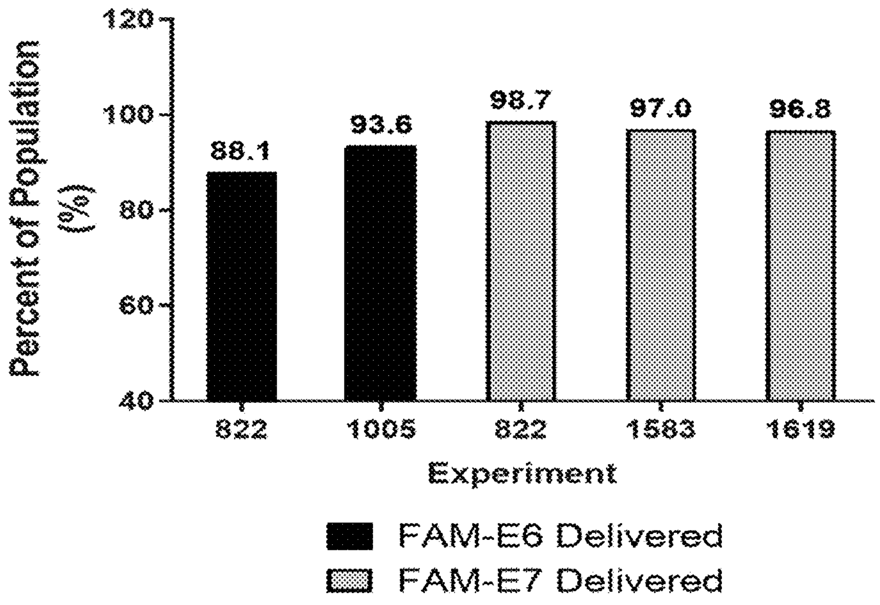
FIG. 5 shows delivery of FAM-labeled E6 and E7 peptides following passage of red blood cells through a chip a different cell concentrations.

FIG. 5 shows the % of population to which FAM-E6 SLP and FAM-E7 SLP were delivered to be >88% and >96% respectively.

Figure 6:
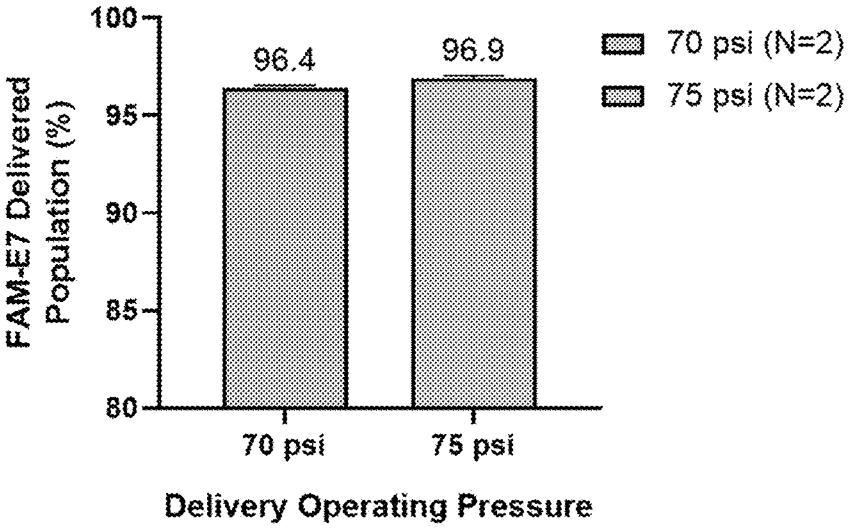
FIG. 6 shows delivery of FAM-labeled E7 peptides following passage of red blood cells through a chip at different pressures.

Reduced Operating Pressure for Peptide (E6 and E7 SLPs) & Adjuvant (Poly I:C) Delivery Two studies were performed using the same donor whole blood delivered with FAM-labeled E7 peptide at 70 psi, with a 75 psi control to compare delivery. The results are shown in FIG. 6.

The results from these experiments demonstrated that the lower operating pressure of 70 psi resulted in equivalent FAM-E7 delivery as the 75 psi operating pressure. As a result of this evaluation, the target operating pressure for delivery of peptide and adjuvant was changed to 70 psi.

The final delivery parameters selected are shown in Table 4.

TABLE 4

Delivery Process Parameters

| Target Operating Pressure | Target Operating Temperature | Microfluidic Chip Configuration |
|---|---|---|
| 70 psi | 2-8 °C | 4 × 2.2 μm constriction chips in parallel |

Poly I:C content was measured from SQZ-AAC-HPV drug product vials after the development of delivery process parameters were completed. Results from representative batches are shown in Table 5.

TABLE 5

Poly I:C Content across Representative Full Process Runs

| Experiment # | Sample | AAC concentration ($\times10^9$ AACs/mL) | Total poly I:C concentration (μg/$10^9$ AACs) |
|---|---|---|---|
| 2257 - arm A | SQZ-AAC-HPV | 0.91 | 10.0 |
| 2357 - arm 116FA | SQZ-AAC-HPV | 1.02 | 10.3 |
| 2357 - arm 117FA | SQZ-AAC-HPV | 0.98 | 11.5 |

Product Resting (37 °C Incubation)

Following the 30-minute ambient resting step of the Peptide & Adjuvant Delivery process, the AACs are diluted, and then further rested by placing on a rocker inside an incubator at 37 °C for 2 hours. To determine these parameters, evaluations of rest time and pre-rest dilution volume were performed.

Studies were performed comparing 1-hour and 2-hour rest times and comparing rest with diluted AACs (diluted with RPMI media) and undiluted AACs. These studies measured for stepwise recovery over the rest period and % population of AACs in the final drug product. The results of these evaluations showed an improvement in recovery when AACs were rested for 2 hours in comparison to the 1-hour rest.

Additional evaluations were performed with product resting of diluted vs undiluted AACs. The functional response of the respective drug product from each study condition was evaluated.

Figure 7:
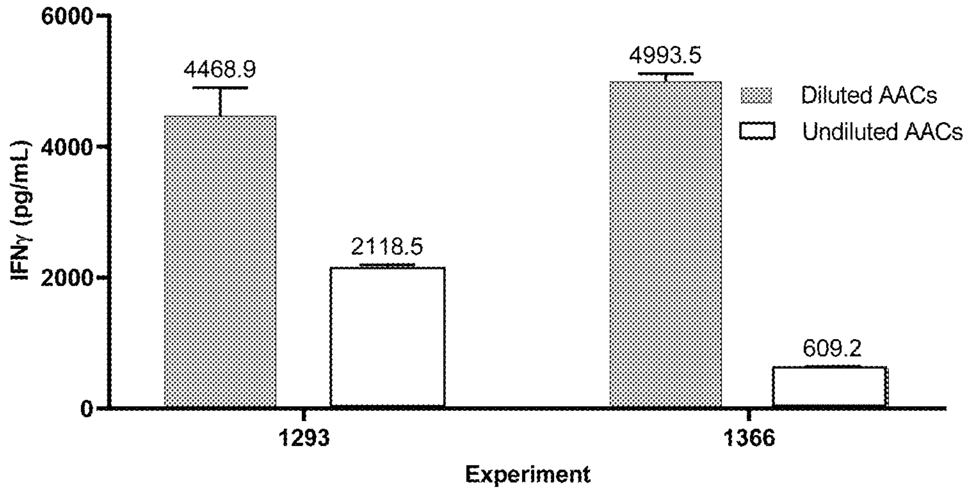
FIG. 7 shows a functional analysis as measured by IFNγ levels when AACs are diluted or undiluted AACs during a 37 °C rest period.

The data reported in FIG. 7 show a significantly higher secreted IFN-γ levels when diluted AACs are rested compared to undiluted AACs that are rested in the process. Based on this evaluation, a 1 L dilution of the delivered AACs prior to the 37 °C rest was implemented into the manufacturing process.

The average AAC recovery over the product rest step across n=15 studies was analyzed to be 93.6%. This data demonstrates that high AAC recovery is achieved with the parameters evaluated and implemented for incubation (Table 6).

TABLE 6

Product Resting Parameters

| Dilution media | Dilution volume | Incubation time | Incubation temperature |
|---|---|---|---|
| RPMI | 1 L | 120 ± 10 minutes | 37 ± 1 °C |

AAC-HPV Drug Substance Count for Clinical Manufacturing

Due to continuous processing, minimal in-process hold time of the AAC-HPV drug substance is desired. To enable this, samples are obtained from the in-process AACs prior to the Product Resting step. During the 2-hour rest, the samples are analyzed, and the count measured with a correction factor of 0.9 is used to calculate the total AACs in the final AAC-HPV drug substance. The 0.9 correction factor was established considering the average incubation stepwise recovery of 93.7% (rounded down to 90%) observed during development.

After rest, the delivered AACs are gravity filtered through a sterile single-use 40 μm blood filter. Following the 40 μm filtration, the drug substance is washed and exchanged into the final formulation media using the LOVO.

Whole Blood Hold Time

Whole blood hold time is defined as the end time of whole blood collection (i.e., end of patient blood draw) to the start of the whole blood dilution (start of manufacturing). The initial evaluation of the whole blood hold time was performed with hold times of 36 and 50 hours at 2-°C. The studies consisted of splitting one healthy donor blood unit and using one half to produce SQZ-AAC-HPV following a 1-day hold (approximately 24 hours) for the control arm, and the other half following a 36- or 50-hour hold. The resultant SQZ-AAC-HPV drug products were analyzed for functional response. Product made from aged whole blood using either hold time (36 or 50 hours) elicits a functional response within assay and process variability similar to that of the control (24 hour). As a conservative approach, 36 hours was implemented as the whole blood hold time for the patient starting material. This hold time may be extended as more data are generated to support longer hold times.

Example 2. Drug Product Formulation

The drug product, SQZ-AAC-HPV, is prepared by formulating the AAC-HPV drug substance in CryoStor® CS2, to target a concentration of $7.0\times10^{8}$ AACs/mL (as analyzed using a Coulter-based cell counter (Moxi GO II)), accounting for AAC losses during the formulation step, and filling into vials. The vials are cryopreserved using a controlled-rate freezer with a chamber temperature of ≤−170 °C, with the vials reaching and maintaining a temperature of ≤−140 °C during production, storage and shipment.

Post-thaw AAC recoveries confirm that this cryopreservation media is suitable for the SQZ-AAC-HPV drug product.

The following evaluations were performed to develop the drug product formulation process.

Verification of LOVO System Parameters for Drug Product Formulation

An initial LOVO protocol (Protocol 1) was developed with guidance from the equipment vendor (Fresenius Kabi). The aim of this protocol was to achieve a high theoretical washout (i.e., buffer media exchange) over the process of 99.97%. This was enabled by creating a maximum outlet packed cell volume (outlet PCV) as given by the following equation:

$$\text{outlet PCV}=(\text{inlet flow rate}\div\text{outlet flow rate})\times\text{inlet PCV}.$$

The LOVO Protocol 1 parameters are listed in Table 7 below.

TABLE 7

LOVO Protocol 1 Processing Parameters for Final Drug Product Formulation

| Cycle | Spinner Rate (rpm) | Inlet Flow Rate (mL/min) | Outlet Flow Rate (mL/min) | Inlet PCV | Outlet PCV | Final Output Volume (mL) |
|---|---|---|---|---|---|---|
| Cycle 1 | 4000 | 100 | 20 | 10.5 | 52.5 | 800 |
| Cycles 2-5 | 4000 | 88 | 25 | 10.5 | 36.9 | 800 |
| Cycle 6 | 4000 | 100 | 15 | 10.5 | 70 | Input Dependent |

Figure 8:
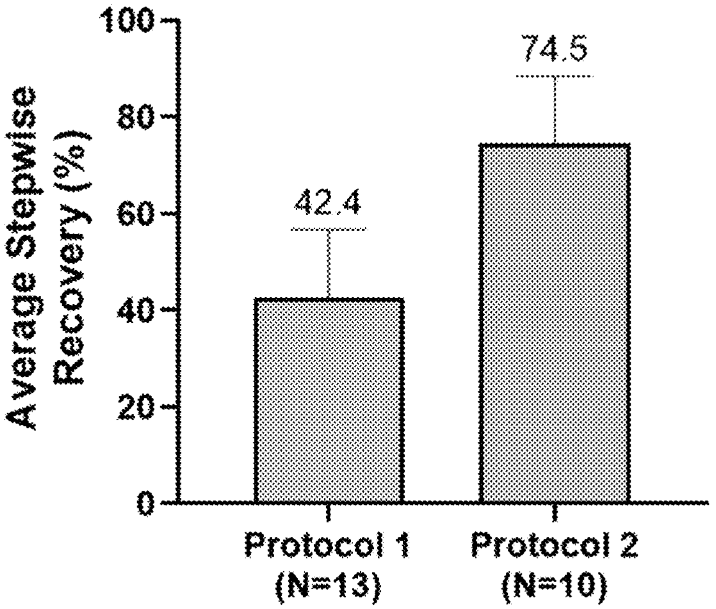
FIG. 8 shows average recovery rates for LOVO processing using two different protocols.

After evaluating Protocol 1 over n=13 experiments with material from 8 donors, the average stepwise recovery observed was 42.4%, as shown in FIG. 8. The low recoveries observed over the formulation step significantly impacted the manufacturing process yield. As a result of the low recoveries, a second LOVO protocol was evaluated with the aim of increasing manufacturing process yield.

For Protocol 2, the LOVO processing parameters were adjusted to target a lower maximum outlet PCV of 36% for all 6 wash cycles to improve recovery while maintaining a high theoretical washout of 99.96%. The LOVO Protocol 2 parameters can be found in Table 8 below. The protocol was implemented in n=10 experiments with material from 8 different donors, and the average AAC recovery increased to 74.5%, as shown in FIG. 8. Due to the improved recovery, Protocol 2 was selected to be used for clinical manufacturing of SQZ-AAC-HPV.

TABLE 8

LOVO Protocol 2 Processing Parameters for Final Drug Product Formulation

| Cycle | Spinner Rate (rpm) | Inlet Flow Rate (mL/min) | Outlet Flow Rate (mL/min) | Inlet PCV | Outlet PCV | Final Output Volume (mL) |
|---|---|---|---|---|---|---|
| Cycle 1-5 | 4000 | 88 | 25 | 10.5 | 36.9 | 800 |
| Cycle 6 | 4000 | 88 | 25 | 10.5 | 36.9 | Input Dependent |

Figure 9:
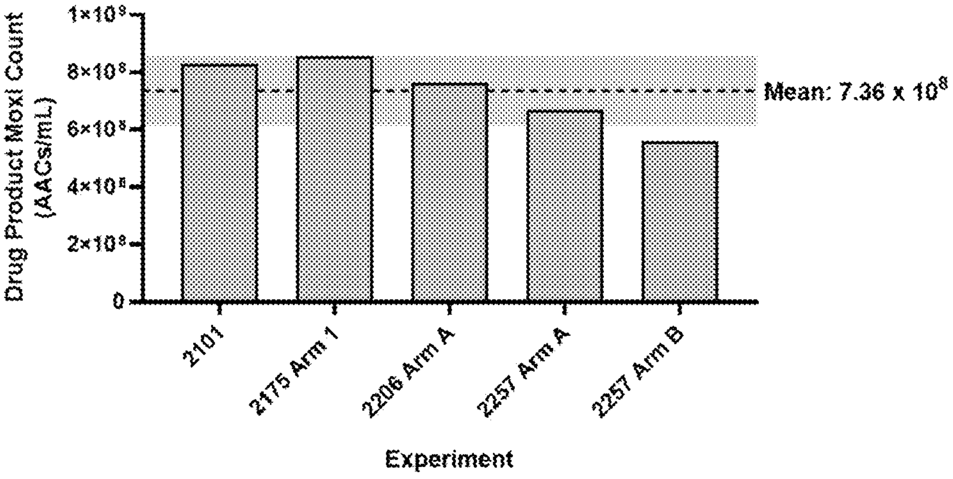
FIG. 9 shows LOVO processing to achieve a target concentration of $7\times10^8$ AACs/mL.

The LOVO processing parameters were finalized to those shown in Table 8, and were used during full scale process development studies, with the results shown in FIG. 9. These results demonstrate that a target concentration of $7\times10^{8}$ AACs/mL at final formulation is achievable with these LOVO parameters.

Vial Filling, Inspection, and Labeling

Vial filling is performed inside a biosafety cabinet. Vials are supplied sterile, fully stoppered, and ready to use. For filling, each vial is filled with 9.98 g±5% of product (i.e., 9.5 mL, which allows for an extractable volume of 8.9 mL). Following filling, each vial is sealed, checked for weight, and subsequently capped. Once vial filling is completed, each filled vial is visually inspected for any visible defects (including large clumps or aggregates) using an inspection booth equipped with an illuminated black and white background. Subsequently, each vial is labeled with a cryogenic label.

Process performance capability (Ppk) evaluations were performed for the filling process. The minimum filling Ppk achieved across the tech transfer batches was 4.66 indicating that the filling process is robust and in control. Results of this analysis is provided in Table 9.

TABLE 9

Filling Ppk

| Batch Number | No. of Vials Filled | Target Vial Fill Weight (g) | Average Vial Fill Weight (g) | Upper Specification Limit (USL) (g) | Lower Specification Limit (LSL) (g) | Ppk[1] |
|---|---|---|---|---|---|---|
| 2020_0084 | 62[2] | 9.98 | 9.96 | 10.48 | 9.48 | 5.77 |
| 2020_0070 | 44 | | 9.92 | | | 5.91 |
| 2020_0071 | 36 | | 9.92 | | | 7.87 |
| 2020_0072 | 52 | | 9.93 | | | 4.66 |

[1]Ppk = Minimum Value of: (USL − Mean)/3*σ) or (Mean − LSL)/(3*σ)

[2]Total vials filled is 62 vials, 1 vial was rejected due to visible particulates Cryopreservation and Storage The secondary storage boxes containing the labeled SQZ-AAC-HPV vials are loaded onto a rack inside the controlled-rate freezer, and subsequently cryopreserved to a product temperature of ≤140 °C. Following cryopreservation, vials are provided to QC for release, characterization, stability testing and retains and placed in an isothermal $LN_2$ tank for long term storage. The remaining cryopreserved vials are kept in the labeled secondary storage boxes and placed in an isothermal $LN_2$ tank for long term storage.

Figure 10:
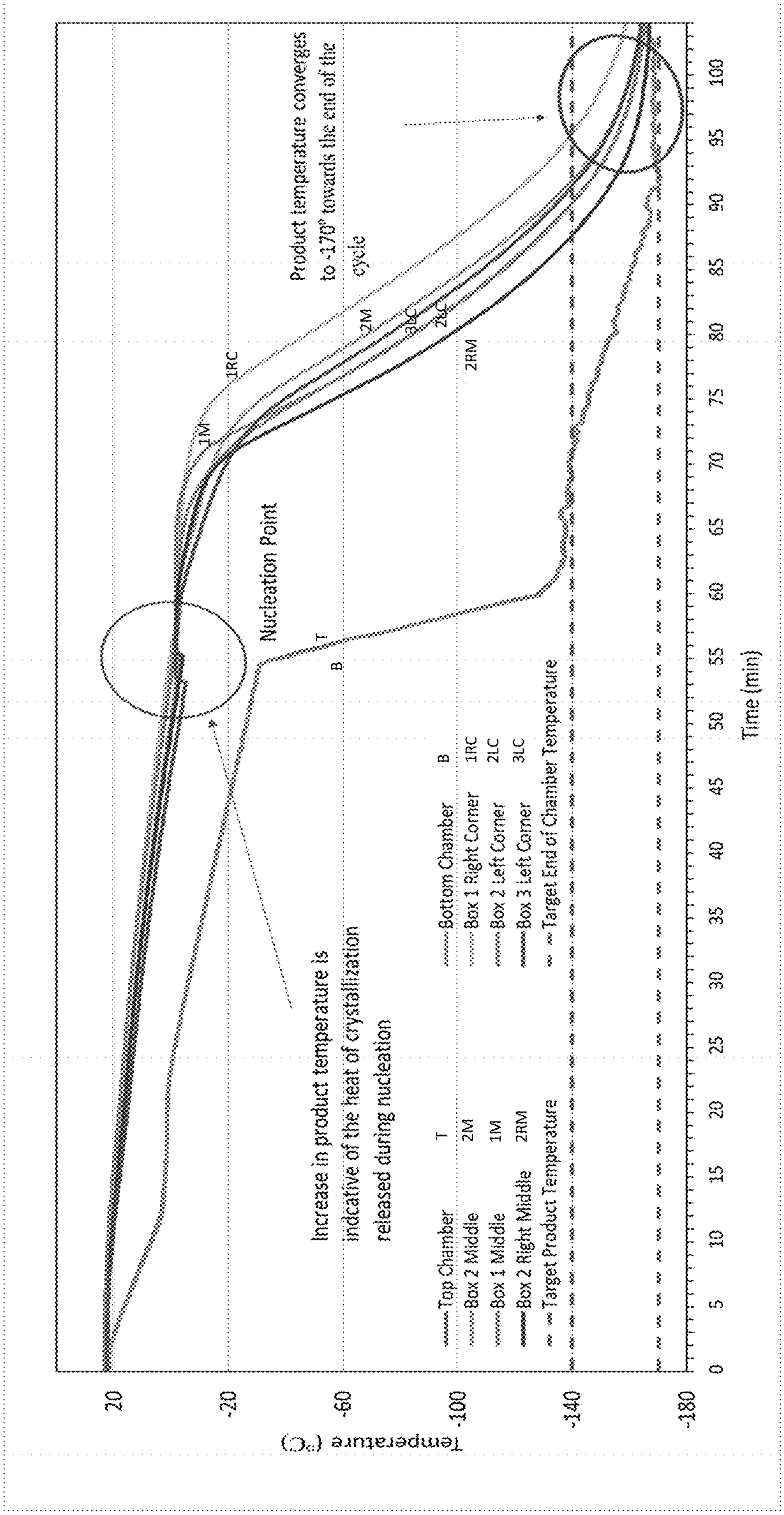
FIG. 10 shows a representative load of 48 vials of SQZ-AAC-HPV being cryopreserved using the developed protocol.
Figure 11:
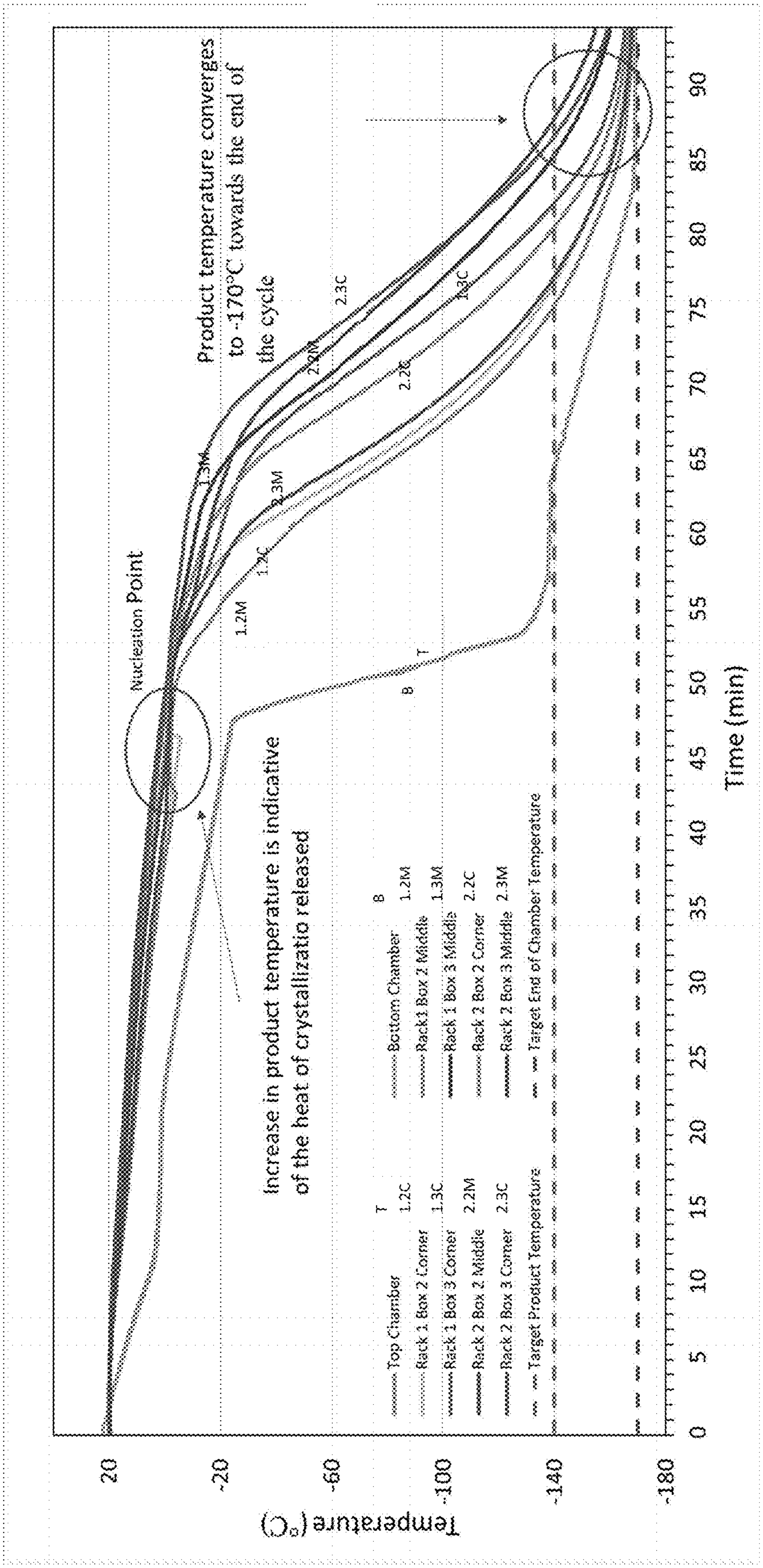
FIG. 11 shows a representative load of 64 vials of SQZ-AAC-HPV being cryopreserved using a two-rack configuration.

A CryoMed® controlled-rate freezer with a 34 L chamber capacity and a custom cryopreservation protocol were used to cryopreserve the SQZ-AAC-HPV drug product. The custom freezing profile has been designed to control the latent heat released during nucleation of the drug product. Ice nucleation in the drug product is initiated at approximately −5 °C. To control the latent heat released during nucleation of the drug product, rapid cooling of the chamber must be initiated prior to the product temperature reaching the nucleation point (−5 °C). During cryopreservation of SQZ-AAC-HPV, the chamber temperature is rapidly cooled to −140 °C at a cooling rate of −20 °C/min after the product temperature reaches −3 °C which is slightly above the nucleation point (−5 °C). Subsequently, the product is cooled to −150 °C at a cooling rate of −1.5 °C/min. Once the product temperature reaches −150 °C, the chamber is cooled to −170 °C at a cooling rate of −1 °C/min and then held at −170 °C for 10 minutes. A maximum chamber load of 64 vials was established for cryopreservation of SQZ-AAC-HPV with one of the vials being used for product temperature monitoring. Details of the cryopreservation protocol are shown in Table 10. Chamber and product temperature profiles resulting from the cryopreservation protocol is shown in FIGS. 10 and 11.

TABLE 10

Controlled-Rate Freezer Protocol for AAC Cryopreservation

| Step | Protocol Parameter |
|---|---|
| 1 | Decrease chamber temperature by −2 °C/min to 0 °C |
| 2 | Hold chamber at 0 °C for 10 minutes |
| 3 | Decrease product temperature by −1 °C/min to −3 °C |
| 4 | Decrease chamber temperature by −20 °C/min to −140 °C |
| 5 | Hold chamber at −140 °C for 10 minutes |
| 6 | Decrease product temperature by −1.5 °C/min to −150 °C |
| 7 | Decrease chamber temperature by −1 °C/min to −170 °C |
| 8 | Hold chamber at −170 °C for 10 minutes |
| 9 | End |

FIG. 10 shows a representative load of 48 vials of SQZ-AAC-HPV being cryopreserved using the developed protocol. As shown in the product temperature traces above, SQZ-AAC-HPV cryopreserved at different locations within the freezing chamber undergo nucleation at a similar time and reach a final product temperature ≤−140 °C prior to completion of the cycle. The total cryopreservation cycle time for the representative chamber load is approximately 100 minutes.

FIG. 11 shows a maximum load of 64 vials of SQZ-AAC-HPV being cryopreserved using a two-rack configuration. As shown FIGS. 10 and 11, SQZ-AAC-HPV placed in both racks at different locations within the freezing chamber undergo nucleation at a similar time and reach a final product temperature ≤−140 °C prior to completion of the cycle. The total cryopreservation cycle time for the maximum chamber load is approximately 95 minutes.

Based on the temperature profiles from both chamber loads, the developed protocol shows a consistent profile can be achieved across all vial loads up to a maximum of 64 vials.

Post Thaw AAC Recovery

To assess stability and recovery of AACs post cryopreservation, the drug product is thawed and tested for AAC count using flow cytometry. It should be noted that an increase in AAC concentration was observed post thaw using flow cytometry analysis as opposed to Coulter-based counting resulting in a higher AAC content per vial at release compared to the manufacturing in-process data. The Moxi GO II, a Coulter-based cell counter, is used to count in-process AAC samples during manufacturing. In contrast, a flow cytometry method is used to identify and count AACs (CD235a+Annexin V+) during QC release of SQZ-AAC-HPV drug product. In-process AAC sample analysis using the less sensitive Moxi GO II counter has a negative bias relative to measurements of the corresponding post-thaw measurements of SQZ-AAC-HPV using the flow cytometry method.

The concentration targeted during the final drug product formulation step is $7.0\times10^{8}$ AACs/mL, and the in-process counts for n=5 process development batches using the Moxi GO II were on average $7.36\times10^{8}$ AACs/mL (see FIG. 9).

Figure 12:
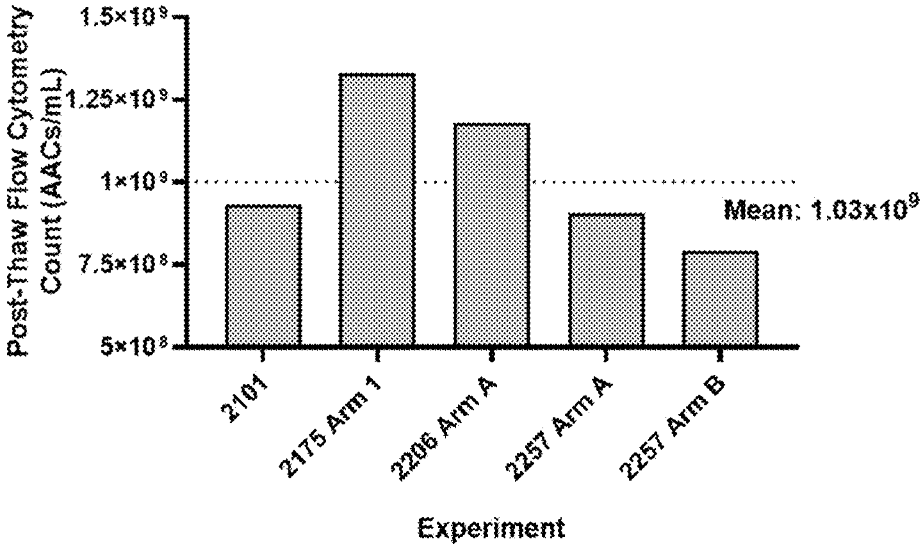
FIG. 12 shows post thaw counts from five process development batches. The average AAC count across these five batches was $1.03\times10^9$ AACs/mL.

The data shown in FIG. 12 report post thaw counts from n=5 process development batches. The average AAC count across these 5 batches was $1.03\times10^{9}$ AACs/mL, showing that the AAC recovery through a freeze thaw cycle in Cryostor® CS2 excipient meets the expected post thaw target concentration of $1.0\times10^{9}$ AACs/mL. The post thaw counts are in line with these results (Table 11).

TABLE 11

| Batch Number | Date of Manufacture | Whole Blood RBC Count (Total Cells) [b] | Drug Product Batch Size (mL) | Batch Size (Vials) | Post Thaw AAC Count (AACs/mL)[c] | Overall Process Recovery[a] |
|---|---|---|---|---|---|---|
| 2020_0084 | 15 Sep. 2020 | $7.17 \times 10^{11}$ | 635 | 61 | $8.83 \times 10^{8}$ | 71.3% |
| 2020_0070 | 29 Sep. 2020 | $7.51 \times 10^{11}$ | 459 | 44 | $1.09 \times 10^{9}$ | 60.7% |
| 2020_0071 | 6 Oct. 2020 | $6.42 \times 10^{11}$ | 370 | 36 | $9.99 \times 10^{8}$ | 53.2% |
| 2020_0072 | 13 Oct. 2020 | $7.66 \times 10^{11}$ | 526 | 52 | $9.62 \times 10^{8}$ | 62.0% |
| Mean | | $7.19 \times 10^{11}$ | 498 | 47 | $9.84 \times 10^{8}$ | 61.8 |
| Range | | $6.42\text{-}7.66 \times 10^{11}$ | 370-635 | 36-61 | $8.83 \times 10^{8}\text{-}1.09 \times 10^{9}$ | 53.2-71.3% |

[a]Overall process recovery = 100% x (vials filled x post-thaw AAC Count x 9.5 mL)/whole blood starting RBC count.

[b] Measured by hematology analyzer.

[c]Measured by flow cytometry method

Based on the average process recovery from whole blood to drug product (61.8%), it is estimated that the tentative minimum RBCs in the whole blood, $5.0\times10^{11}$ total cells, would yield 32 vials of SQZ-AAC-HPV ($5.0\times10^{11}$ RBCs in whole blood×61.8% average process recovery/$9.5\times10^{9}$ target AACs/drug product vial).

SEQUENCES

| SEQ ID NO | Sequence | Description |
|---|---|---|
| 1 | TIHDIILECV | HPV16-E6(29-38), human epitope |
| 2 | EVYDFAFRDL | HPV16-E6(48-57), murine epitope |
| 3 | YMLDLQPETT | HPV16-E7(11-20), human epitope |
| 4 | RAHYNIVTF | HPV16-E7(49-57), murine epitope |
| 5 | LPQL**S**TELQT | HPV16-E6(19-28) N-terminal polypeptide, human |
| 6 | QLCTELQT | HPV16-E6(21-28) N-terminal polypeptide, human |
| 7 | KQQLLRR | HPV16-E6(41-47) N-terminal polypeptide, native murine |
| 8 | VYSKQQLLRR | HPV16-E6(38-47) N-terminal polypeptide, classic murine |
| 9 | MHGDTPTLHE | HPV16-E7(1-10) N-terminal polypeptide, human |
| 10 | GQAEPD | HPV16-E7(43-48) N-terminal polypeptide, murine |
| 11 | Y**S**KQQLLRREVYDFAF | HPV16-E6(39-54) C-terminal polypeptide, human |
| 12 | YCKQQLL | HPV16-E6(39-45) C-terminal polypeptide, human |
| 13 | CIVYRDGN | HPV16-E6(58-65) C-terminal polypeptide, native murine |
| 14 | SIVYRDGNPYAVSDK | HPV16-E6(58-72) C-terminal polypeptide, classic murine |
| 15 | DLYCYEQLNDSSEEE | HPV16-E7(21-35) C-terminal polypeptide, human |
| 16 | CCKCDSTLRLCVQSTHVDIR | HPV16-E7(58-77 C-terminal polypeptide, native murine |
| 17 | SSKSDSTLRLSVQSTHVDIR | HPV16-E7(58-77) C-terminal polypeptide, classic murine |
| 18 | LPQLSTELQTTIHDIILECVYSKQQLLRREVYDFAF | HPV16-E6(19-54) SLP, human |
| 19 | QLCTELQTTIHDIILECVYCKQQLL | HPV16-E6(21-45) SLP, human |
| 20 | KQQLLRREVYDFAFRDLCIVYRDGN | HPV16-E6(41-65) SLP, native murine |
| 21 | VYSKQQLLRREVYDFAFRDLSIVYRDGNPYAVSDK | HPV16-E6(38-72) SLP, classic murine |
| 22 | MHGDTPTLHEYMLDLQPETTDLYCYEQLNDSSEEE | HPV16-E7(1-35) SLP, human |
| 23 | QLCTELQTYMLDLQPETTYCKQQLL | HPV16-E7.6 SLP, human |
| 24 | GQAEPDRAHYNIVTFCCKCDSTLRLCVQSTHVDIR | HPV16-E7(43-77) SLP, native murine |

-continued

SEQUENCES

| SEQ ID NO | Sequence | Description |
|---|---|---|
| 25 | GQAEPDRAHYNIVTFSSKSDSTLRLSVQSTHVDIR | HPV16-E7(43-77) SLP, classic murine |
| 26 | ggGGTCAACGTTGAgggggg<br>Bases shown in capital letters are phosphodiester, and those in lower case are phosphorothioate | ODN 1585 (Class A, mouse-specific) |
| 27 | ggGGGACGA:TCGTCgggggg<br>Bases shown in capital letters are phosphodies-ter, and those in lower case are phosphorothioate | ODN 2216 (Class A, human-selective) |
| 28 | gggGACGAC:GTCGTGgggggg<br>Bases shown in capital letters are phosphodies-ter, and those in lower case are phosphorothioate | ODN 2336 (Class A, human preferred) |
| 29 | tccatgacgttcctgatgct<br>Bases shown in capital letters are phosphodies-ter, and those in lower case are phosphorothioate | ODN 1668 (Class B, mouse specific) |
| 30 | tccatgacgttcctgacgtt<br>Bases are phosphorothioate | ODN 1826 (Class B, mouse specific) |
| 31 | tcgtcgttttgtcgttttgtcgtt<br>Bases are phosphorothioate | ODN 2006 (Class B, human selective) |
| 32 | tcg tcg ttg tcg ttt tgt cgt t<br>Bases are phosphorothioate | ODN 2007 (Class B, bovine/porcine) |
| 33 | tcg acg ttc gtc gtt cgt cgt tc<br>Bases are phosphorothioate | ODN BW006 (Class B, human & mouse) |
| 34 | tcg cga cgt tcg ccc gac gtt cgg ta<br>Bases are phosphorothioate | ODN D-SL01 (Class B, multispecies) |
| 35 | tcgtcgttttcggcgc:gcgccg<br>Bases are phosphorothioate | ODN 2395 (Class C, human/mouse) |
| 36 | tcgtcgtcgttc:gaacgacgttgat<br>Bases are phosphorothioate | ODN M362 (Class C, human/mouse) |
| 37 | tcg cga acg ttc gcc gcg ttc gaa cgc gg<br>Bases are phosphorothioate | ODN D-SL03 (Class C, multispecies) |
| 38 | MHGDTPTLHEYMLDLQPETTDLYCYEQLNDSSEEE | E7 |
| 39 | LYCYEQLNDSSEEEDEIDGPAGQAEPDRAHYNIVT | E7 |
| 40 | GQAEPDRAHYNIVTFCCKCDSTLRLCVQSTHVDIR | E7 |
| 41 | TLRLCVQSTHVDIRTLEDLLMGTLGIVCPICSQKP | E7 |
| 42 | MHQKRTAMFQDPQERPRKLPQLCTELQTTIHD | E6 |
| 43 | LPQLCTELQTTIHDIILECVYCKQQLLRREVY | E6 |
| 44 | KQQLLRREVYDFAFRDLCIVYRDGN | E6 |
| 45 | RDLCIVYRDGNPYAVCDKCLKFYSKI | E6 |
| 46 | DKCLKFYSKISEYRHYCYSLYGTTL | E6 |
| 47 | HYCYSLYGTTLEQQYNKPLCDLLIR | E6 |
| 48 | YGTTLEQQYNKPLCDLLIRCINCQKPLCPEEK | E6 |

-continued

| SEQUENCES | | |
|---|---|---|
| SEQ ID NO | Sequence | Description |
| 49 | RCINCQKPLCPEEKQRHLDKKQRFHNIRGRWT | E6 |
| 50 | DKKQRFHNIRGRWTGRCMSCCRSSRTRRETQL | E6 |

What is claimed is:

1. A pharmaceutical formulation comprising:

a) activating antigen carriers (AACs) derived from input anucleate cells in the absence of heat processing, chemical treatment, being subjected to hypotonic or hypertonic conditions, and/or osmolarity deviations outside of between about 200 mOsm and 600 mOsm, and wherein the AACs comprise anucleate cells and/or vesicles derived therefrom, and comprise at least one antigen and an adjuvant internally, and b) a cryopreservation medium, wherein the formulation comprises: (i) about $0.5\times10^9$ AACs to about $1\times10^{10}$ AACs; or (ii) about $0.5\times10^9$ AACs/mL to about $1\times10^9$ AACs/mL, in the cryopreservation medium, and wherein the cryopreservation medium comprises dimethylsulfoxide (DMSO), and wherein the formulation comprises any one of about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, or about $0.5\times10^9$ to about $1.0\times10^9$ AACs/ml post-thawing.

2. A pharmaceutical formulation comprising:

a) activating antigen carriers (AACs) derived from input anucleate cells in the absence of heat processing, chemical treatment, being subjected to hypotonic or hypertonic conditions, and/or osmolarity deviations outside of between about 200 mOsm and 600 mOsm, and wherein the AACs comprise anucleate cells and/or vesicles derived therefrom, and comprise at least one antigen and an adjuvant internally, and b) a cryopreservation medium, wherein the formulation comprises: (i) about $0.5\times10^9$ AACs to about $1\times10^{10}$ AACs or (ii) about $0.5\times10^9$ AACs/mL to about $1\times10^9$ AACs/mL, in the cryopreservation medium, and wherein at least about 70% of the AACs stain positive for annexin.

3. The pharmaceutical formulation of claim 2, wherein the cryopreservation medium comprises dimethylsulfoxide (DMSO).

4. The pharmaceutical formulation of claim 1, wherein the pH of the formulation is about 6.0 to about 8.5.

5. The pharmaceutical formulation of claim 2, wherein the pH of the formulation is about pH 6.0 to about pH 8.5, and wherein the formulation comprises any one of about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, or about $0.5\times10^9$ to about $1.0\times10^9$ AACs/mL post-thawing.

6. The pharmaceutical formulation of claim 2, wherein the pH of the formulation is about pH 7.6, and wherein the formulation comprises any one of about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, or about $0.5\times10^9$ to about $1.0\times10^9$ AACs/mL post-thawing.

7. The pharmaceutical formulation of claim 1, wherein the formulation comprises about $7\times10^9$ AACs in about 9.5 mL of cryopreservation medium, and wherein the pH of the formulation is about pH 7.6.

8. The pharmaceutical formulation of claim 1, which: (i) is sterile, (ii) comprises less than about 2 EU/mL endotoxin, (iii) is free of mycoplasma, or (iv) any combination of (i) to (iii).

9. The pharmaceutical formulation of claim 1, wherein the at least one antigen comprises one or more human papillomavirus (HPV) antigens.

10. The pharmaceutical formulation of claim 9, wherein the one or more HPV antigens comprise the amino acid sequence of any one of SEQ ID NOs: 1-4 or 18-25.

11. The pharmaceutical formulation of claim 1, wherein the adjuvant comprises a CpG oligodeoxynucleotide (ODN), LPS, IFN-a, STING agonists, RIG-I agonists, poly I:C, R837, R848, a TLR3 agonist, a TLR4 agonist a TLR 9 agonist, or a combination thereof.

12. A vial comprising the pharmaceutical formulation of claim 1.

13. A method of producing a pharmaceutical formulation comprising AACs, the method comprising:

adding a cryopreservation medium to the AACs to formulate the AACs, wherein the AACs are derived from input anucleate cells, and comprise i) anucleate cells and/or vesicles derived therefrom, and ii) comprise at least one antigen and an adjuvant; and freezing the formulation of AACs, wherein the freezing comprises:

a) reducing the temperature of a chamber comprising the formulation of AACs to between about 0 °C and −20 °C, or about −3 °C;

b) reducing the temperature of the chamber to −140 °C±5 °C at a rate of between about −10 °C/minute and −30 °C/minute, or about −20 °C/minute;

c) reducing the temperature of the chamber to −150 °C±5 °C at a rate of between about −0.5 °C/minute and −5 °C/minute, or about −1.5 °C/minute;

d) reducing the temperature of the chamber to −170 °C±15 °C at a rate of between about −0.1 °C/minute and −5 °C/minute, or about −1.0 °C/minute, and e) holding the temperature of the chamber at −170 °C±15 °C for at least about 5 to 30 minutes, or about 10 minutes.

14. The method of claim 13, further comprising:

a) passing a cell suspension comprising input anucleate cells through a cell-deforming constriction, thereby causing perturbations of the input anucleate cells; and b) contacting the perturbed anucleate cells with the at least one antigen and the adjuvant such that the at least one antigen and the adjuvant pass through the perturbations and enter the perturbed anucleate cells, to generate the AACs.

15. The method of claim 14, wherein the diameter of the cell-deforming constriction is about 1.6 μm to about 2.4 μm.

16. The method of claim 13, wherein about $1\times10^{9}$ AACs to about $1\times10^{10}$ AACs are formulated in about 9 mL to about 10 mL of the cryopreservation medium.

17. The method of claim 14, wherein the input anucleate cells comprise red blood cells.

18. A method of introducing an immune response in a subject in need thereof, comprising administering to the subject the pharmaceutical formulation of claim 1.

* * * * *

SEQUENCE LISTING

<160> NUMBER OF SEQ ID NOS: 50

<210> SEQ ID NO 1
<211> LENGTH: 10
<212> TYPE: PRT
<213> ORGANISM: Human papilloma virus

<400> SEQUENCE: 1

Thr Ile His Asp Ile Ile Leu Glu Cys Val
1               5                   10

<210> SEQ ID NO 2
<211> LENGTH: 10
<212> TYPE: PRT
<213> ORGANISM: Human papilloma virus

<400> SEQUENCE: 2

Glu Val Tyr Asp Phe Ala Phe Arg Asp Leu
1               5                   10

<210> SEQ ID NO 3
<211> LENGTH: 10
<212> TYPE: PRT
<213> ORGANISM: Human papilloma virus

<400> SEQUENCE: 3

Tyr Met Leu Asp Leu Gln Pro Glu Thr Thr
1               5                   10

<210> SEQ ID NO 4
<211> LENGTH: 9
<212> TYPE: PRT
<213> ORGANISM: Human papilloma virus

<400> SEQUENCE: 4

Arg Ala His Tyr Asn Ile Val Thr Phe
1               5

<210> SEQ ID NO 5
<211> LENGTH: 10
<212> TYPE: PRT
<213> ORGANISM: Human papilloma virus

<400> SEQUENCE: 5

Leu Pro Gln Leu Ser Thr Glu Leu Gln Thr
1               5                   10

<210> SEQ ID NO 6
<211> LENGTH: 8
<212> TYPE: PRT
<213> ORGANISM: Human papilloma virus

<400> SEQUENCE: 6

```
Gln Leu Cys Thr Glu Leu Gln Thr
1               5


<210> SEQ ID NO 7
<211> LENGTH: 7
<212> TYPE: PRT
<213> ORGANISM: Human papilloma virus

<400> SEQUENCE: 7

Lys Gln Gln Leu Leu Arg Arg
1               5


<210> SEQ ID NO 8
<211> LENGTH: 10
<212> TYPE: PRT
<213> ORGANISM: Human papilloma virus

<400> SEQUENCE: 8

Val Tyr Ser Lys Gln Gln Leu Leu Arg Arg
1               5                   10


<210> SEQ ID NO 9
<211> LENGTH: 10
<212> TYPE: PRT
<213> ORGANISM: Human papilloma virus

<400> SEQUENCE: 9

Met His Gly Asp Thr Pro Thr Leu His Glu
1               5                   10


<210> SEQ ID NO 10
<211> LENGTH: 6
<212> TYPE: PRT
<213> ORGANISM: Human papilloma virus

<400> SEQUENCE: 10

Gly Gln Ala Glu Pro Asp
1               5


<210> SEQ ID NO 11
<211> LENGTH: 16
<212> TYPE: PRT
<213> ORGANISM: Human papilloma virus

<400> SEQUENCE: 11

Tyr Ser Lys Gln Gln Leu Leu Arg Arg Glu Val Tyr Asp Phe Ala Phe
1               5                   10                  15


<210> SEQ ID NO 12
<211> LENGTH: 7
<212> TYPE: PRT
<213> ORGANISM: Human papilloma virus

<400> SEQUENCE: 12

Tyr Cys Lys Gln Gln Leu Leu
1               5


<210> SEQ ID NO 13
<211> LENGTH: 8
<212> TYPE: PRT
<213> ORGANISM: Human papilloma virus

<400> SEQUENCE: 13

Cys Ile Val Tyr Arg Asp Gly Asn
```

1 5

<210> SEQ ID NO 14
<211> LENGTH: 15
<212> TYPE: PRT
<213> ORGANISM: Human papilloma virus

<400> SEQUENCE: 14

Ser Ile Val Tyr Arg Asp Gly Asn Pro Tyr Ala Val Ser Asp Lys
1 5 10 15

<210> SEQ ID NO 15
<211> LENGTH: 15
<212> TYPE: PRT
<213> ORGANISM: Human papilloma virus

<400> SEQUENCE: 15

Asp Leu Tyr Cys Tyr Glu Gln Leu Asn Asp Ser Ser Glu Glu Glu
1 5 10 15

<210> SEQ ID NO 16
<211> LENGTH: 20
<212> TYPE: PRT
<213> ORGANISM: Human papilloma virus

<400> SEQUENCE: 16

Cys Cys Lys Cys Asp Ser Thr Leu Arg Leu Cys Val Gln Ser Thr His
1 5 10 15

Val Asp Ile Arg
20

<210> SEQ ID NO 17
<211> LENGTH: 20
<212> TYPE: PRT
<213> ORGANISM: Human papilloma virus

<400> SEQUENCE: 17

Ser Ser Lys Ser Asp Ser Thr Leu Arg Leu Ser Val Gln Ser Thr His
1 5 10 15

Val Asp Ile Arg
20

<210> SEQ ID NO 18
<211> LENGTH: 36
<212> TYPE: PRT
<213> ORGANISM: Artificial Sequence
<220> FEATURE:
<223> OTHER INFORMATION: Synthetic Construct

<400> SEQUENCE: 18

Leu Pro Gln Leu Ser Thr Glu Leu Gln Thr Thr Ile His Asp Ile Ile
1 5 10 15

Leu Glu Cys Val Tyr Ser Lys Gln Gln Leu Leu Arg Arg Glu Val Tyr
20 25 30

Asp Phe Ala Phe
35

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Gln Leu Cys Thr Glu Leu Gln Thr Thr Ile His Asp Ile Ile Leu Glu
1               5                   10                  15

Cys Val Tyr Cys Lys Gln Gln Leu Leu
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 21
<211> LENGTH: 35
<212> TYPE: PRT
<213> ORGANISM: Artificial Sequence
<220> FEATURE:
<223> OTHER INFORMATION: Synthetic Construct

<400> SEQUENCE: 21

Val Tyr Ser Lys Gln Gln Leu Leu Arg Arg Glu Val Tyr Asp Phe Ala
1               5                   10                  15

Phe Arg Asp Leu Ser Ile Val Tyr Arg Asp Gly Asn Pro Tyr Ala Val
            20                  25                  30

Ser Asp Lys
        35

<210> SEQ ID NO 22
<211> LENGTH: 35
<212> TYPE: PRT
<213> ORGANISM: Artificial Sequence
<220> FEATURE:
<223> OTHER INFORMATION: Synthetic Construct

<400> SEQUENCE: 22

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Leu Cys Thr Glu Leu Gln Thr Tyr Met Leu Asp Leu Gln Pro Glu
1               5                   10                  15

Thr Thr Tyr Cys Lys Gln Gln Leu Leu
            20                  25

<210> SEQ ID NO 24
<211> LENGTH: 35
<212> TYPE: PRT
<213> ORGANISM: Artificial Sequence
<220> FEATURE:
<223> OTHER INFORMATION: Synthetic Construct

<400> SEQUENCE: 24

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 25
<211> LENGTH: 35
<212> TYPE: PRT
<213> ORGANISM: Artificial Sequence
<220> FEATURE:
<223> OTHER INFORMATION: Synthetic Construct

<400> SEQUENCE: 25

Gly Gln Ala Glu Pro Asp Arg Ala His Tyr Asn Ile Val Thr Phe Ser
1               5                   10                  15

Ser Lys Ser Asp Ser Thr Leu Arg Leu Ser Val Gln Ser Thr His Val
            20                  25                  30

Asp Ile Arg
        35

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggggtcaacg ttgagggggg                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
gggggacgat cgtcgggggg                                                  20

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ggggacgacg tcgtgggggg g                                                21

<210> SEQ ID NO 29
<211> LENGTH: 20
<212> TYPE: DNA
<213> ORGANISM: Artificial Sequence
<220> FEATURE:

<223> OTHER INFORMATION: Synthetic Construct

<400> SEQUENCE: 29
tccatgacgt tcctgatgct 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
tccatgacgt tcctgacgtt 20

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct

<400> SEQUENCE: 31
tcgtcgtttt gtcgttttgt cgtt 24

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tcgtcgttgt cgttttgtcg tt 22

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
tcgacgttcg tcgttcgtcg ttc 23

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
tcgcgacgtt cgcccgacgt tcggta 26

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
tcgtcgtttt cggcgcgcgc cg 22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
tcgtcgtcgt tcgaacgacg ttgat 25

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct

<400> SEQUENCE: 37
tcgcgaacgt tcgccgcgtt cgaacgcgg 29

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

Met His Gly Asp Thr Pro Thr Leu His Glu Tyr Met Leu Asp Leu Gln
1 5 10 15

Pro Glu Thr Thr Asp Leu Tyr Cys Tyr Glu Gln Leu Asn Asp Ser Ser
20 25 30

Glu Glu Glu
35

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct

<400> SEQUENCE: 39

Leu Tyr Cys Tyr Glu Gln Leu Asn Asp Ser Ser Glu Glu Glu Asp Glu
1 5 10 15

Ile Asp Gly Pro Ala Gly Gln Ala Glu Pro Asp Arg Ala His Tyr Asn
20 25 30

Ile Val Thr
35

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

Gly Gln Ala Glu Pro Asp Arg Ala His Tyr Asn Ile Val Thr Phe Cys
1 5 10 15

Cys Lys Cys Asp Ser Thr Leu Arg Leu Cys Val Gln Ser Thr His Val
20 25 30

Asp Ile Arg
35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

```
Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35
```

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30
```

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

```
Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30
```

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

```
Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25
```

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

```
Arg Asp Leu Cys Ile Val Tyr Arg Asp Gly Asn Pro Tyr Ala Val Cys
```

1 5 10 15

Asp Lys Cys Leu Lys Phe Tyr Ser Lys Ile
20 25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

Asp Lys Cys Leu Lys Phe Tyr Ser Lys Ile Ser Glu Tyr Arg His Tyr
1 5 10 15

Cys Tyr Ser Leu Tyr Gly Thr Thr Leu
20 25

<210> SEQ ID NO 47
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

His Tyr Cys Tyr Ser Leu Tyr Gly Thr Thr Leu Glu Gln Gln Tyr Asn
1 5 10 15

Lys Pro Leu Cys Asp Leu Leu Ile Arg
20 25

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Tyr Gly Thr Thr Leu Glu Gln Gln Tyr Asn Lys Pro Leu Cys Asp Leu
1 5 10 15

Leu Ile Arg Cys Ile Asn Cys Gln Lys Pro Leu Cys Pro Glu Glu Lys
20 25 30

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Arg Cys Ile Asn Cys Gln Lys Pro Leu Cys Pro Glu Glu Lys Gln Arg
1 5 10 15

His Leu Asp Lys Lys Gln Arg Phe His Asn Ile Arg Gly Arg Trp Thr
20 25 30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

-continued

```
Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30
```